(12) United States Patent
O'Brien et al.

(10) Patent No.: US 8,799,022 B1
(45) Date of Patent: Aug. 5, 2014

(54) METHOD AND NETWORK FOR SECURE TRANSACTIONS

(75) Inventors: James W. O'Brien, Tampa, FL (US); Charles L. Laye, Tampa, FL (US)

(73) Assignee: Strat ID GIC, Inc., Tampa, FL (US)

( * ) Notice: Subject to any disclaimer, the term of this patent is extended or adjusted under 35 U.S.C. 154(b) by 194 days.

(21) Appl. No.: 13/464,786

(22) Filed: May 4, 2012

Related U.S. Application Data

(60) Provisional application No. 61/518,379, filed on May 4, 2011.

(51) Int. Cl.
 *G06Q 50/22* (2012.01)

(52) U.S. Cl.
 USPC .................................................. 705/3; 705/2

(58) Field of Classification Search
 None
 See application file for complete search history.

(56) References Cited

U.S. PATENT DOCUMENTS

| | | | |
|---|---|---|---|
| 5,956,400 | A | 9/1999 | Chaum et al. |
| 6,283,761 | B1 * | 9/2001 | Joao .............................. 434/236 |
| 6,397,224 | B1 | 5/2002 | Zubeldia et al. |
| 6,442,687 | B1 | 8/2002 | Savage |
| 6,874,085 | B1 | 3/2005 | Koo et al. |
| 6,990,491 | B2 | 1/2006 | Dutta et al. |
| 7,039,810 | B1 | 5/2006 | Nichols |
| 7,088,823 | B2 | 8/2006 | Fetkovich |
| 7,103,915 | B2 | 9/2006 | Redlich et al. |
| 7,158,979 | B2 | 1/2007 | Iverson |
| 7,165,175 | B1 | 1/2007 | Kollmyer et al. |
| 7,237,268 | B2 | 6/2007 | Fields |
| 7,254,837 | B2 | 8/2007 | Fields |
| 7,310,651 | B2 | 12/2007 | Dave et al. |
| 7,322,047 | B2 | 1/2008 | Redlich et al. |
| 7,349,987 | B2 | 3/2008 | Redlich et al. |
| 7,380,120 | B1 | 5/2008 | Garcia |
| 7,383,183 | B1 | 6/2008 | Davis et al. |
| 7,386,575 | B2 | 6/2008 | Bashant et al. |
| 7,391,865 | B2 | 6/2008 | Orsini et al. |
| 7,404,079 | B2 * | 7/2008 | Gudbjartsson et al. ....... 713/168 |
| 7,418,474 | B2 | 8/2008 | Schwab |
| 7,437,550 | B2 | 10/2008 | Savage et al. |
| 7,451,315 | B2 | 11/2008 | Coltrera |
| 7,461,006 | B2 * | 12/2008 | Gogolak ........................... 705/2 |
| 7,480,622 | B2 | 1/2009 | Dutta et al. |
| 7,484,245 | B1 | 1/2009 | Friedman et al. |
| 7,496,669 | B2 * | 2/2009 | Hirayama ..................... 709/229 |

(Continued)

FOREIGN PATENT DOCUMENTS

JP 2000299702 A * 10/2000 ............. H04L 12/56

*Primary Examiner* — Michael Fuelling
*Assistant Examiner* — Michael Tomaszewski
(74) *Attorney, Agent, or Firm* — Frijouf, Rust & Pyle, P.A.

(57) ABSTRACT

An apparatus and method for a secure transaction and communication network between a multitude of enrolled enterprises and customers. An enrollment database outputs an authenticated identity to an encounter database that generates an encounter number that it outputs to an enrolled establishment for generating a transaction order to a transaction database. A transmission server assigns serial numbers to encrypt each transmission. Serial number A from the enrollment server is tagged to the identity information and serial B from the transaction database is tagged to the data information and each is sent separately to both the supplier and the encounter server. The encounter server matches Serial A and B to create the first rule data set that the supplier uses to match the order data to the identity records to complete the secure transmission of the de-identified transaction information and arrange for it's re-identification at the supplier's location.

19 Claims, 24 Drawing Sheets

(56) References Cited

U.S. PATENT DOCUMENTS

| | | |
|---|---|---|
| 7,496,767 B2 | 2/2009 | Evans |
| 7,509,487 B2 | 3/2009 | Lu et al. |
| 7,512,986 B2 | 3/2009 | Shen-Orr et al. |
| 7,519,591 B2 | 4/2009 | Landi et al. |
| 7,543,149 B2 | 6/2009 | Ricciardi et al. |
| 7,546,334 B2 | 6/2009 | Redlich et al. |
| 7,552,482 B2 | 6/2009 | Redlich et al. |
| 7,668,835 B2 | 2/2010 | Judd et al. |
| 7,702,755 B2 | 4/2010 | Schwab |
| 7,725,716 B2 | 5/2010 | Tidwell et al. |
| 8,473,313 B2 * | 6/2013 | Abreu ............... 705/3 |
| 8,498,879 B2 * | 7/2013 | Michon et al. ........ 705/2 |
| 2001/0056359 A1 * | 12/2001 | Abreu ............... 705/3 |
| 2002/0010679 A1 * | 1/2002 | Felsher ............. 705/51 |
| 2002/0116227 A1 * | 8/2002 | Dick ............... 705/3 |
| 2003/0021417 A1 | 1/2003 | Vasic et al. |
| 2004/0143594 A1 | 7/2004 | Kalies |
| 2005/0165623 A1 | 7/2005 | Landi et al. |
| 2009/0076847 A1 * | 3/2009 | Gogolak ............ 705/2 |

\* cited by examiner

METHOD AND NETWORK FOR SECURE TRANSACTIONS

CROSS-REFERENCE TO RELATED APPLICATIONS

This application claims benefit of U.S. Patent Provisional application Ser. No. 61/518,379 filed May 4, 2011. All subject matter set forth in provisional application Ser. No. 61/518,379 is hereby incorporated by reference into the present application as if fully set forth herein.

BACKGROUND OF THE INVENTION

1. Field of the Invention

This invention relates to a network system and more particularly to a secure computer network system.

2. Background of the Invention

The advent of computers has lead to the electronic management of banking and finance transactions and records in past years with great success. One of the greatest problems facing these systems is file integrity and protection from unauthorized access. Encryption and encoding methodologies have been developed to help maintain the security of these information systems. Over time these encryption and encoding schemes had to evolve to more complicated levels to stay ahead of the continual advancements in hardware and computer software that threatened to provide decryption and decoding capabilities to undermine the security these systems once provided. 64 bit encryption/encoding platform gave way to 128 bit encryption encoding platform and yielded to a 256 bit encryption/encoding platform, which is currently under assault and must inevitable give way to a 512 bit platform that will eventually fail as well. The strength of these security systems is based on their level of complexity and as technology advances these levels are eventually overcome. These information systems will never be secure for any length of time if they continue to depend on encryption and encoding schemes as the foundation of their security strategies. The medical community's interest in adopting electronic medical records has encouraged the development of security strategies for that industry that do not depend entirely on encryption and encoding.

The medical community has relied on written medical records and handwritten medical prescriptions which the patient would hand carry to the pharmacist for filling. More recently, the medical community has begun to use computer systems for medical records and prescriptions. In addition to the file integrity and protection problems similar to the finance industry problems, HIPPA (health Insurance Portability and Accountablity Act) has set a national standard for the protection of medical records.

Boosted by a multi-billion dollar federal stimulus, the medical community is moving toward paperless, computer based medical and prescription systems. Multi-port access for a plurality of contributing medical professionals and multi-port access to data from a plurality of authorized record and prescription requestors presents substantial challenges to the design and implementation of these systems. Data integrity and protection and assuring the confidentiality of both record content and identity of the record owner remains a significant problem for these systems.

There have been many in the prior art who have attempted to solve these problems in the medical and financial community with varying degrees of success. None, however completely satisfies the requirements for a complete solution to the aforestated problem. The following U.S. Patents are attempts of the prior art to solve this problem.

U.S. Pat. No. 5,946,400 to Chaum, et al. discloses an information storage system including one or more information update terminals, a mapper, one or more partial-databases, and one or more query terminals, exchanging messages over a set of communication channels. An identifier-mapping mechanism provides (to an update terminal) a method for delegating control over retrieval of the data stored at the partial-databases to one or more mappers, typically operated by one or more trusted third parties. Update terminals supply information, that is stored in fragmented form by the partial-databases. Data-fragment identifiers and pseudonyms are introduced, preventing unauthorized de-fragmentation of information—thus providing compliance to privacy legislation—while at the same time allowing query terminals to retrieve (part of) the stored data or learn properties of the stored data. The mapper is necessarily involved in both operations, allowing data access policies to be enforced and potential abuse of stored information to be reduced. Introduction of multiple mappers acts to distribute information retrieval control among multiple trusted third parties. Introducing so-called 'groupers' increases the efficiency of data retrieval for a common set of queries and further reduces potential abuse of information.

U.S. Pat. No. 6,397,224 to Zubeldia, et al. discloses a system for anonymously linking a plurality of data records. Each data record comprises a plurality of elements for identifying an associated individual, including a first identity reference encoding module configured to encode a first encoded identity reference from a first subset of the identifying elements of a data record and a second identity reference encoding module configured to encode a second encoded identity reference from a second subset of the identifying elements of the data record. An anonymization code assignment module configured to assign to each of the first and second encoded identity references an identical anonymization code for anonymously representing the individual associated with the data record.

U.S. Pat. No. 6,442,687 to Savage discloses a system providing secure and anonymous communications over a network, which is accomplished by imposing mechanisms that separate users' actions from their identity. In one embodiment, involving use of the Internet, an http request, which normally contains both identity and action information, is separated in the first instance on the client side into action request and identity components, which are encrypted. The encrypted action and identity components are transmitted to a facility comprising an "identity server" and an "action server", wherein the identity server receives the two encrypted request components and forwards the encrypted action request component to an action server. The identity server has the key to decrypt the identity component (but not the action component), and the action server has the key to decrypt the action component (but not the identity component). The action server decrypts the action request and forwards it to the third-party server. The third-party server sends the http response back to the action server. The action server receives and encrypts the action response, and forwards it to the identity server. The identity server, which has been holding the unencrypted user identity information, receives the encrypted action response (which it cannot decipher), and forwards it to the client system, wherein the user's browser software uses the action response in the normal manner, so as to create the appropriate displays and/or multimedia output.

U.S. Pat. No. 6,874,085 to Loo, et al. discloses a system whereby a medical record is partitioned into personal and medical data portions, and an identification code is concatenated into each portion. The personal data portion is encrypted so a patient's identity cannot be linked to the patient's medical data except by authorized viewers. Each portion of the secure medical record can be transferred over a network as separate files, and stored in a data storage system separately. Access to the entire medical record is thereby provided only to those who know the key for the personal data portion of the medical record. The system and method can be used to help ensure patient confidentiality while allowing patient medical records to be accessed over a network such as the Internet, providing physicians and patients quick access to their medical records. The system and method can be used to create a database of anonymous medical records useful for medical research.

U.S. Pat. No. 6,990,491 to Dutta, et al. discloses a system and method for data maintenance and privilege authorization. An accessibility database server receives an accessibility record request from a requestor that includes a user identifier and a requestor identifier. The requestor identifier may correspond to a user, a healthcare practitioner server, an insurance server, a transcoding proxy server, a portal server, a web server, an advertisement server, or a service provider. The accessibility database server compares the accessibility record request with the requestor's access permission to determine whether the requestor has access corresponding to the particular request. If the requestor is authorized for the particular request, the accessibility database server processes the accessibility record request.

U.S. Pat. No. 7,039,810 to Nichols discloses a system whereby sensitive data such as patient records are securely transferred between a programmer and a data encryption. A database residing on the programmer contains patient information obtained by at least one implantable medical device. A key source provides the programmer with a first key and the remote expert data center with a second key to be used in the encryption/decryption process. An encryption engine residing within the programmer encrypts the sensitive patient information contained within the database, using the first key. The programmer transmits the encrypted patient information to the remote expert data center via a data communications system such as a public network. A decryption engine residing within the remote expert data center decrypts the encrypted sensitive patient information using the second key.

U.S. Pat. No. 7,088,823 to Fetkovich discloses a method for controlling access to digital information based on a plurality of decryption keys sent by the information provider. A first type of decryption key instructs a user's host system to reproduce the digital information in accordance with a first level of reproduction quality degradation. Additional keys may specify other degradation levels. The quality of the digital information may be degraded based on a time condition or a use condition. Alternatively, only a portion of the information may be made viewable by a user. In order to obtain full and unrestricted access, the user must obtain a type of decryption key from the provider which removes all previous limitations on reproduction quality degradation.

U.S. Pat. No. 7,103,915 to Redlich, et al. discloses a method for securing data including establishing a group of security sensitive items, filtering data and extracting and separating the security items from remainder data. The filtered data are separately stored (locally on a PC or on another computer in a LAN or WAN or on the Internet.) A map may be generated. The filter and/or map may be destroyed or stored. The data input, extracted data and remainder data may be deleted from the originating computer. Encryption may be utilized to enhance security (including transfers of data, filter and map). Reconstruction of the data is permitted only in the presence of a predetermined security clearance. A plurality of security clearances may be used to enable a corresponding plurality of partial, reconstructed views of the plaintext (omitting higher security words). A computer readable medium containing programming instructions and an information processing system is encompassed.

U.S. Pat. No. 7,158,979 to Iverson, et al. discloses a method of de-identifying data, wherein the data to be de-identified is stored in a transaction table containing transactions and a personal information table containing identifiable information. The method includes the steps of generating a de-identification pointer associated with an individual in the personal information table, wherein the individual is associated with at least one transaction in the transaction table; creating a non-protected transaction table, wherein the non-protected transaction table includes a non-protected transaction reference and non-protected information associated with a transaction from the transactional table; and creating an index table including the identification and the non protected transaction reference. According to a preferred embodiment, the identification is advantageously unique and may also lack context to the individual. According to a further feature, the identification may be random or pseudo-random.

U.S. Pat. No. 7,165,175 to Kollmyer, et al. discloses an apparatus and method for selectively encrypting portions of data sent over a network between a server and a client. The apparatus includes parsing means for separating a first portion of the data from a second portion of the data, encrypting means for encrypting only of the first portion of the data, and combining means for combining the encrypted first portion of the data with the second portion of the data, wherein the second portion of the data is not encrypted. The apparatus further includes decrypting means installed at the client for decrypting the encrypted portion of the data. The apparatus is platform independent in terms of media format and data protocol. The encryption unit encrypts data transparently to the client based on the media format. The apparatus of the invention is implemented as one of an application and a plug-in object. The method for selectively encrypting portions of data which differ from each other in at least on characteristic sent over a network between a server and a client includes parsing the data into a first and second portion, encrypting only the first portion of the data, and sending the encrypted first portion and the second portion of the data over the network to the client. The method further includes receiving data from the server, determining whether a data stream is established between the server and the client, and negotiating an encryption key with a decryption shim of the client.

U.S. Pat. No. 7,237,268 to Fields discloses a method and system for providing a type of Managed/Secured File Transfer between one or more computers arraigned in server-client or peer-to-peer configuration. This method and system takes digital content in the form of a file, shreds this file into separate pieces and encrypts each piece separately. Once encrypted, each piece is stored into a database. Client applications can then access these pieces of digital content over a network, decrypt and reassemble each piece to be played in the case of audio/video content, or viewed in the case of visual content. In some embodiments, the content requested by the client application is stored into a second database in a shredded and encrypted format, whereas in other embodiments the content is reassembled into the original non-encrypted and non-shredded file format. This method and system can reside on a computer system, hand held device, or other device.

U.S. Pat. No. 7,254,837 to Fields discloses a method and system for providing a type of Managed/Secured File Transfer between one or more computers arraigned in server-client or peer-to-peer configuration. This method and system takes digital content in the form of a file, shreds this file into separate pieces and encrypts each piece separately. Once encrypted, each piece is stored into a database. Client applications can then access these pieces of digital content over a network, decrypt and reassemble each piece to be played in the case of audio/video content, or viewed in the case of visual content. In some embodiments, the content requested by the client application is stored into a second database in a shredded and encrypted format, whereas in other embodiments the content is reassembled into the original non-encrypted and non-shredded file format. This method and system can reside on a computer system, hand held device, or other device.

U.S. Pat. No. 7,310,651 to Dave, et al. discloses a medical communications and management system (MCMS) that is operative to compile, store, retrieve and transmit digitized medical information from a variety of medical imaging modalities, as well as digital information such as scanned in images, digital photographs, audio files, and digitized information corresponding to monitored physiological conditions, such as heart rate and the like. The MCMS is further operative to include personal patient identification information, such as retinal scans and fingerprints, and is capable of being archived to thus enable such digitized information to be readily accessed. To that end, it is contemplated that the MCMS of the present invention will be used in connection with an electronic medical record and facilitate compliance with HIPAA.

U.S. Pat. No. 7,322,047 to Redlich, et al. discloses a data security method, system and associated data mining enabling multiple users, each having a respective security clearance level to access security sensitive words, data objects, characters or icons. The method extracts security sensitive words, data objects, characters or icons from plaintext or other source documents to obtain (a) subsets of extracted data and (b) remainder data. The extracted data is, in one embodiment, stored in a multilevel security system (MLS) which separates extract data of different security levels with MLS guards. Some or all of the original data is reconstructed via one or more of the subsets of extracted data and remainder data only in the presence of a predetermined security level. In this manner, an inquiring party, with the proper security clearance, can data mine the data in the MLS secured storage.

U.S. Pat. No. 7,349,987 to Redlich, wet al. discloses a data security system having parsing and dispersion aspects enabling the user to parse, disperse and reconstruct the original, plain text data or data object, thereby enabling secure storage of the data. The original data may be maintained in its original state, encrypted or it may be destroyed. For example, financial data maintained by an institute, stored as is customary, be parsed with an algorithm, the parsed segments dispersed off-site (that is, separated and stored in extract and remainder stores or computer memories) and away from the financial institute, and, upon appropriate security clearance, the dispersed data can be reconstructed to duplicate the data. Large distribution of parsed data is contemplated by the system. The original data remains stable, operable and immediately useful in its customary storage location (or alternatively destroyed). The secured dispersed data is a back-up of the original data.

U.S. Pat. No. 7,380,120 to Garcia discloses a system for providing access control management to electronic data, techniques to secure the electronic data and keep the electronic data secured at all times. According to one embodiment, a secured file or secured document includes two parts: an attachment, referred to as a header, and an encrypted document or data portion. The header includes security information that points to or includes the access rules and a file key. The access rules facilitate restrictive access to the secured document and essentially determine who/when/how/where the secured document can be accessed. The file key is used to encrypt/decrypt the encrypted data portion. Only those who have the proper access privileges are permitted to retrieve the file key to encrypt/decrypt the encrypted data portion.

U.S. Pat. No. 7,383,183 to Davis, et al. discloses systems and methods for transcribing private information. The method, includes receiving a first information segment during a first interview session, and receiving a second information segment during a second interview session, wherein the first information segment A includes private information and the second information segment includes only non-private information. The exemplary method also includes providing information in the first information segment to a first transcriber, providing information in the second information segment to a second transcriber, wherein the second transcriber has no communication with the first transcriber. The exemplary method further includes providing a combination of the information transcribed from the first and second information segments to a user or other recipient authorized to receive the private information.

U.S. Pat. No. 7,386,575 to Bashant et al. discloses a system and method for tracking and synchronizing related data elements in disparate storage systems. More particularly, the present invention provides a hub system for cross-referencing and maintaining storage system information for the efficient synchronization of related data elements in disparate storage systems.

U.S. Pat. No. 7,391,865 to Orsini, et al. discloses an invention providing a method and system for securing sensitive data from unauthorized access or use. The method and system of the present invention is useful in a wide variety of settings, including commercial settings generally available to the public which may be extremely large or small with respect to the number of users. The method and system of the present invention is also useful in a more private setting, such as with a corporation or governmental agency, as well as between corporation, governmental agencies or any other entity.

U.S. Pat. No. 7,404,079 to Gudbjartsson, et al. discloses an invention providing an automated system for the processing of data packets, composed of personal identifiers and personal data, such that the personally identifiable data sent by one party may be considered anonymous once received by a second party. The invention uses secret sharing techniques to facilitate distributed key management of the mapping functions and strong authentication to allow the system to be operated remotely.

U.S. Pat. No. 7,418,474 to Schwab discloses methods and apparatus which provide secure interactive communication of text and image information between a central server computer and one or more client computers located at remote sites for the purpose of storing and retrieving files describing and identifying unique products, services, or individuals. Textual information and image data from one or more of the remote sites are stored separately at the location of the central server computer, with the image data being in compressed form, and with the textual information being included in a relational database with identifiers associated with any related image data. Means are provided at the central computer for management of all textual information and image data received to ensure that all information may be independently retrieved. Requests are entered from remote terminals specifying particular subject matter, and the system is capable of responding to multiple simultaneous requests. Textual information is recalled and downloaded for review, along with any subsequently requested image data, to be displayed at a remote site. Various modes of data and image formatting are also disclosed, including encryption techniques to fortify data integrity. The server computers may be interfaced with other computers to effect financial transactions, and images representing the subjects of transactions may be uploaded to the server computer to create temporary or permanent records of financial or legal transactions. A further feature of the system is the ability to associate an identification image with a plurality of accounts, transactions, or records.

U.S. Pat. No. 7,437,550 to Savage, et al. discloses an invention providing secure and private communication over a network, as well as persistent private storage and private access control to the stored information, which is accomplished by imposing mechanisms that separate a user's actions from their identity. The system provides (i) anonymous network browsing, in which event the anonymity system is unaware of both the user's identity and browsing activities, (ii) private network storage and retrieval of data such as passwords, profiles and files in a manner such that the data can be stored into the system and later retrieved without the system knowing the contents or owners of the data, and (James W. O'Brien & Charles L. Layc) the ability of the user to control and manage access to the remotely stored data without the system knowing the contents, owners, or accessors of the data.

U.S. Pat. No. 7,451,315 to Coltrera discloses a system whereby data input from multiple sites are collected and shared, using identifiers to maintain a link to sensitive portions of the data that were collected, without initially sharing the sensitive data. Unique record identifiers and parsed structure data information (PSD-Info) are used in connection with a checksum when sharing information without disclosing all of the sensitive data. Any shared subset data and the PSD-Info are encrypted with a private key and transmitted to a data recipient, who decrypts the information with a public key, verifying the identity of the sender. If later agreed by the parties, the sensitive data can be similarly transmitted. Maintaining a link between the shared information and the sensitive data that are withheld for confidential and privacy reasons provides proof for audit purposes, without disclosing the withheld data.

U.S. Pat. No. 7,480,622 to Dutta, et al. discloses a system for accessibility insurance coverage management. An insurance server receives a coverage request from a requestor that includes a user identifier corresponding to a user (i.e. policyholder). The insurance server matches the user identifier with a stored policyholder identifier and retrieves accessibility data corresponding to the matched policyholder identifier. If required, the insurance server updates the policyholder's accessibility data by receiving accessibility data from an accessibility database server. The insurance server identifies the policyholder's coverage using the user's accessibility data along with the user's policy information. The insurance server sends a message to the requestor which indicates an amount of the particular item corresponding to the coverage request the insurance server covers. The insurance server receives accessibility service bills on a frequent basis, such as monthly. The insurance server verifies the billing information, pays the bill, and updates policyholder claims paid to date information.

U.S. Pat. No. 7,484,245 to Friedman, et al. discloses a system and method for protecting the security of data. The data is packaged together with one or more permissions that designate what actions are allowed with respect to the data. The package can be opened when there is approval for doing so and the allowed permissions are maintained. The data is stored within a vault and there are a number of available security procedures that prevent the unauthorized access of the data.

U.S. Pat. No. 7,496,669 to Hirayama discloses an apparatus for transferring the title of content to an ID-assigning unit which assigns an ID to the content and transmits the content ID to a broadcasting unit via a tagging unit. A broadcasting apparatus then broadcasts the content ID and a receiver extracts the content ID from a received signal and transfers the content ID to a verification unit which determines whether or not the content ID received from a reception functional unit matches a stored content ID. If the content ID received from the reception unit matches a stored content ID, user information of the receiver is transmitted to a privacy-guarding unit. The privacy-guarding unit searches privacy-guarding items and, in accordance with a result of the search, only necessary user information presented by the verification unit is transmitted to a provider unit.

U.S. Pat. No. 7,496,767 to Evans discloses a secure content object protecting electronic documents from unauthorized use. The secure content object includes an encrypted electronic document, a multi-key encryption table having at least one multi-key component, an encrypted header and a user interface device. The encrypted document is encrypted using a document encryption key associated with a multi-key encryption method. The encrypted header includes an encryption marker formed by a random number followed by a derivable variation of the same random number. The user interface device enables a user to input a user authorization. The user authorization is combined with each of the multi-key components in the multi-key encryption key table and used to try to decrypt the encrypted header. If the encryption marker is successfully decrypted, the electronic document may be decrypted. Multiple electronic documents or a document and annotations may be protected by the secure content object.

U.S. Pat. No. 7,509,487 to Lu, et al. discloses secure communication between a resource-constrained device and remote network nodes over a network with the resource-constrained acting as a network node. The remote network nodes communicate with the resource-constrained device using un-modified network clients and servers. Executing on the resource-constrained device, a communications module implements one or more link layer communication protocols, operable to communicate with a host computer, operable to communicate with remote network nodes and operable to implement network security protocols thereby setting a security boundary inside the resource-constrained device.

U.S. Pat. No. 7,512,986 to Shen-Orr et al. discloses a system and a method for providing variable security mechanisms for securing digital content, in which a single security mechanism is not used for all content. Instead, at least one characteristic or feature of the security mechanism is varied between units, instances or categories of content. Therefore, even if unauthorized access is gained to a single unit of content, the overall integrity and security of the system for content distribution is not compromised. Preferably, security is provided through a general mechanism, which is then varied in order to provide variable, dissimilar security schemes for different types of content. By "type of content", it is meant any of a single unit of content, a single instance of content or a single category of content. For example, for a category of content, the content may be characterized according to the identity of the content itself, such as the title of a movie for example, and/or according to the owner of a particular copy of the content. Thus, different security schemes may optionally and preferably be generated from a particular root structure. Related apparatus and methods are also provided.

U.S. Pat. No. 7,519,591 to Landi, et al. discloses systems and methods for protecting individual privacy (e.g., patient privacy) when individual data records (e.g., patient data records) are shared between various entities (e.g., healthcare entities). In one aspect, systems and methods are provided which implement secured key encryption for de-identifying patient data to ensure patient privacy, while allowing only the owners of the patient data and/or legally empowered entities to re-identify subject patients associated with de-identified patient data records, when needed.

U.S. Pat. No. 7,543,149 to Ricciardi, et al. discloses a method for securing patient identity comprising accessing an electronic medical records database including patient data for a plurality of patients. Each patient in the electronic medical records database is assigned a unique patient identifier. Patient data for a first patient, including a first patient identifier, is retrieved from the electronic medical records database. The first patient is de-identified from the patient data. De-identifying includes the creation of a first encoded patient identifier responsive to the first patient identifier. The de-identifying results in de-identified first patient data and includes the replacement of the first patient identifier with the first encoded patient identifier. The de-identified first patient data is transmitted to a data warehouse system. The method further comprises identifying a second patient in response to receiving report data that includes a second encoded patient identifier from the data warehouse system. The identifying includes the creation of a second patient identifier responsive to the second encoded patient identifier.

U.S. Pat. No. 7,546,334 to Redlich, et al. discloses a method, program and information processing system for filtering and securing data (security sensitive words-characters-data objects) in a source document. The adaptive filter uses a compilation of additional data (typically networked) and identifies the sensitive words/objects in the compilation of additional data, and retrieves contextual, semiotic and taxonomic words/objects from the compilation related to the sensitive words/objects. The resulting compiled filter is used to extract sensitive words/objects and retrieved data (words/objects) from the source document to obtain extracted data and remainder data therefrom. Contextual words, related to the security sensitive words/objects, are based upon statistical analysis of the additional data compilation. Semiotic words related words are synonyms, antonyms, and pseudonyms, syntactics relative to the target words and retrieved words, and pragmatics relative to the sensitive words and retrieved words.

U.S. Pat. No. 7,552,482 to Redlich, et al. discloses a method for securing data on a personal computer having security sensitive content grouped into security levels, each with a clearance code, includes filtering and extracting sensitive content by security level and separately storing the security content in remote extract stores. Remainder data is stored locally or remotely. A map for selected extract stores may be generated. The filter and/or map may be destroyed or stored. The data input, extracted data and remainder data may be deleted from the originating computer. Encryption may be utilized to enhance security (including transfers of data, filter and map). Reconstruction of the data is permitted only in the presence of a predetermined security clearance. Full or partial reconstruction is possible, based upon the security clearances. A computer readable medium containing programming instructions and an information processing system is encompassed.

U.S. Pat. No. 7,668,835 to Judd, et al. discloses a method of managing medical information. The method comprises the steps of receiving medical information in a format incompatible with the World Wide Web and converting the medical information to a format compatible with the World Wide Web. Further, the medical information is physically stored at a single location.

U.S. Pat. No. 7,702,755 to Schwab discloses methods and apparatus which provide secure interactive communication of text and image information between a central server computer and one or more client computers located at remote sites for the purpose of storing and retrieving files describing and identifying unique products, services, or individuals. Textual information and image data from one or more of the remote sites are stored separately at the location of the central server computer, with the image data being in compressed form, and with the textual information being included in a relational database with identifiers associated with any related image data. Means are provided at the central computer for management of all textual information and image data received to ensure that all information may be independently retrieved. Requests are entered from remote terminals specifying particular subject matter, and the system is capable of responding to multiple simultaneous requests. Textural information is recalled and downloaded for review, along with any subsequently requested image data, to be displayed at a remote site. Various modes of data and image formatting are also disclosed, including encryption techniques to fortify data integrity. The server computers may be interfaced with other computers to effect financial transactions, and images representing the subjects of transactions may be uploaded to the server computer to create temporary or permanent records of financial or legal transactions. A further feature of the system is the ability to associate an identification image with a plurality of accounts, transactions, or records.

U.S. Pat. No. 7,725,716 to Tidwell, et al. discloses methods and systems for securely requesting, retrieving, sending, and storing files. One aspect involves receiving a request for a file from a client device that identifies a user and the client device, encrypting the file using a session key based at least in part on the user and the client device, and transmitting the encrypted file to the client device. Other aspects of the invention include storing the encrypted file on the client device in encrypted form such that the file may only be decrypted or accessed by the particular user on that particular client device.

United States Patent Application 2002/0116227 to Dick discloses a method for searching for medical information executed by one or more computers. The invention comprises the steps of formulating a request for medical information concerning an individual or group of individuals, transmitting a record request to a record facilitator, the record facilitator determining which patient record sources to investigate, a record query being sent from the facilitator to the patient record sources which are appropriate, receiving a patient record report back from the patient record sources, normalizing and augmenting the patient record report before forwarding it back to the requester, and de-identifying the patient record to remove any identifying information.

United States Patent Application 2003/0021417 to Vasic, et al. discloses a computer system that contains cryptographic keys and cryptographic key identifiers. The system has a repository cryptographic engine that communicates securely with a remote cryptographic engine, and the repository cryptographic engine is associated with a user data store. The user data store includes a hidden link including a session key identifier encrypted with a protection key. The hidden link is associated with a remote data entity. A key data store associated with the repository server includes a session key encrypted with a session-key-protection key. The session key is used to encrypt and decrypt the remote data entity. The system also includes a repository key exchange module operable to exchange the session key with a remote key exchange module.

United States Patent Application 2004/0143594 to Kalies discloses a method for compiling, storing and organizing data, and gathering and reporting medical intelligence derived from patient-specific data. A patient's Minimum Data Set ("MDS") data generated by health care facilities are merged with that patient's pharmacy data to create a comprehensive clinical/pharmacological data set for each patient. The data may first be encrypted to ensure patient privacy before being transmitted by the facility to a data repository via an electronic communication network. Upon receipt at the data repository, the data first must pass through a security screen. If the data is determined to be valid and virus-free, it is decrypted as necessary before being added to a data warehouse for use in a wide variety of therapeutic, statistical, and economic analyses. The data may be partially or completely "de-identified" to remove patient-identifying information so as to protect patient privacy.

United States Patent Application 2005/0165623 to Landi, et al. discloses systems and methods for protecting individual privacy (e.g., patient privacy) when individual data records (e.g., patient data records) are shared between various entities (e.g., healthcare entities). In one aspect, systems and methods are provided which implement secured key encryption for de-identifying patient data to ensure patient privacy, while allowing only the owners of the patient data and/or legally empowered entities to re-identify subject patients associated with de-identified patient data records, when needed.

Although the aforementioned prior art have contributed to the development of the art of electronic medical records systems that generally meets the record keeping needs of the individual medical establishments they fail to meet the medical record keeping needs of the individual patients. This is due in large part to the fact that these patents were designed to rely on the historical documentation or records that were generated by and originally designed for the medical establishments that created them. These information systems were designed to meet the needs of the individual medical establishment's they were created for. They were not designed to create a medical record from the patient's perspective. The doctor's records are the product of the medical information system designed to meet the needs of the doctor. The pharmacists records were designed to meet the needs of the pharmacist. The insurance companies records were designed to meet the insurance company's requirements. Copying parts of the doctor's records the pharmacist's records and the insurance company's records is not the same as designing a system to create the unique vantage point of the patient's record keeping requirements. The copy solution is flawed for the following reasons:

1. Redundant Information

When a doctor writes a prescription for a patient instructing a pharmacist to fill a medicine that will in part be paid by an insurance company we have a four party Medical transaction. All four parties record the transaction in their own way to make sure each completes it's part in the transaction. Providing the patient with a copy of this transaction in the body of a copy of each party's overall medical records for this patient will saddle the patient with at least three separate notations of this single event. This event will be buried somewhere in text of the information provide by each party and it would take a great deal of human effort to track down these redundancies, identify them and then correctly eliminate the duplications.

2. Incomplete Information

There is no overriding structure in place to make sure that every party involved in the care of this patient has provided their copy of what transpired for the patient. Reviewing the parties that provided information to determine which party if any is not represented in the body of work provided would take a great deal of human effort to research and compile.

3. Diverse Information Formats

There is no overriding structure in place to make reliable comparisons of the information provided by each party. Organizing patient information that is in text form that has been created by different information systems is a time consuming task requiring a lot of human intervention. Information systems that do not capture or provide the information in a computer accessible data format make any attempt to access and use the information a major undertaking that requires considerable human intervention.

4. Compilation of Historical Records Versus Recording the Transaction Process.

Creating a patient record by assembling the historical records that were created by each of the medical establishments that provided services for the patient will at best provide a patchwork quilt solution that suffers from the problems identified in 1 through 3 above. The patents reviewed above all begin with historical records. The medical records of these establishments are compilations of each encounter or transaction the patient had with that medical establishment. De identifying the compiled record of transactions to provide security or protection in the process of moving or communicating the patient's historical medical information is like locking the barn after the horse has left the building. It does nothing to provide security to the event that created the transaction or to the transaction itself as it occurs. This is the deficiency in the prior work that this invention intends to address. De identifying the transaction process as it occurs provides security to the transaction itself that the prior art fails to address and recording that de identified data as it is created in such a way as it can be re identified by those intended to have access to it produces a natural de identified patient centered record that is truly the patient's vantage point.

Therefore, it is an object of the present invention to provide an improved system apparatus or platform for the retention of and access to transaction information to allow the creation of a truly patient centered medical record information system.

Another object of this invention is to provide an information system based on recording live transactions in real time rather than attempting to manipulate historical records after the fact.

Another object of this invention is to provide an information system designed to receive inputs from and interact with every commercially viable communication methodology to facilitate recording all patient contacts and communications.

Another object of this invention is to deploy the same security strategies to all contacts and communications rather than focusing entirely on the traditionally recorded event where money changes hands.

Another object of this invention is to create a listing of enrolled individuals and organizations that permits any other enrolled member to choose the method of contacting the other member without revealing the contact details. Selecting the member and the contact method initiates the phone call or the e-mail without revealing the number dialed or the e-mail address of the other party. The party to be contacted will have the option to accept the communication now, latter, or to refuse it indefinitely at their discretion.

Another object of this invention is to collect transaction information in a form acceptable to data base manipulation that will allow computerized research of the information and allow cross links to other industry data bases for advanced research and development.

Another object of this invention is to collect transaction information in the normal course of business transactions that might indicate potentially dangerous or epidemic situations may occur or have already begun in such a manner that allows the immediate notification of the proper authorities without divulging the identities of the parties involve but providing all the profile or demographic information available about them to these authorities so they make take prudent action to protect the common welfare.

Another object of this invention is to provide an improved system and apparatus for ensuring the protection of the identities of all the participants in the transactions within the system that does not rely on encryption and encoding schemes that will fail as technology advances.

Another object of this invention is to provide a transaction platform capable of accepting any commercially acceptable form of payment such as credit card processing or direct checking account debits and credits in a manner that does not reveal the identity of the other transacting party, the transaction date or the amount of any particular transaction to the payment processor.

Another object of this invention is to facilitate a method of sending two communications one perhaps by mail or delivery and the other by c-mail or fax where each contains half of the information required to securely retrieve a data file from an unidentified secret e-mail location on the dark web. The secret e-mail location would have been assigned to the intended recipient upon enrollment and would only allow the recipient access from the recipient's registered computer when both parts of the two communications are combined.

Another object of this invention is to facilitate the identification of enrolled callers to an enrolled establishment's IVR platform so that the caller's voice mail experience can be customized based on knowing their identity and anticipating the purpose of their call.

Another object of this invention is to list all the communication mediums readily available to the party being contacted to allow the system to send a message alerting the intended party of a communication awaiting them that can not be delivered via the current available options for communicating.

Another object of this invention is to allow enrolled employees as part of their enrollment the opportunity to List their name, title, company name and address as they would normally provide in a standard business letter. The system would create a unique barcode to assign to this list of information that would be printed on this employee's snail mailed correspondences, delivered items, faxed materials, inter office memos and embedded into emails and file downloads. When these items are received and if required scanned the barcodes are machine read allowing for the automated delivery of these material to the intended party's I/Ocombox.

Another object of this invention is to provide an improved system and apparatus that provides profile and demographic database information creating the opportunity to link data bases across multiple industries while ensuring the individual privacy of all the participants.

The foregoing has outlined some of the more pertinent objects of the present invention. These objects should be construed as being merely illustrative of some of the more prominent features and applications of the invention. Many other beneficial results can be obtained by modifying the invention within the scope of the invention. Accordingly other objects in a full understanding of the invention may be had by referring to the summary of the invention, the detailed description describing the preferred embodiment in addition to the scope of the invention defined by the claims taken in conjunction with the accompanying drawings.

SUMMARY OF THE INVENTION

The present invention is defined by the appended claims with specific embodiments being shown in the attached drawings. For the purpose of summarizing the invention, the invention relates to an improved method and apparatus for a secure transaction and communications network. The network comprises a first access terminal located at an enrolled establishment for inputting an identity. A second access terminal located at an enrolled customers location for entering an identity. A third supplier terminal located at the establishment of an enrolled supplier to receive the secure transaction communications. A transmission server assigns a unique serial number to each network transmission that it uses to generate a different encryption scheme for each transmission. The transmission server controls how the data in each transmission is packaged and thereafter handled as it is sent over the secured socket layer connection to network destinations. An enrollment database receives, records, searches and outputs the identity of an enrolled individual from an enrolled establishment. An encounter database receives the identity from the enrollment database and assigns it to a transaction order for generating, storing and outputting an encounter number associated with the identity. The first access terminal in the enrolled establishment receives the encounter number from the encounter database and assigns it to a transaction order. The encounter number and the associated order number and order details are sent to a transaction data server from the first access terminal. The transaction data server receives and records the order and the encounter number from the first access terminal for outputting a first data pack and a second data pack. The serial number assigned by the transmission server to encrypt the first data pack prior to transmission is used in the body of both the first and second data packs and is referred to herein as serial B. The first data pack includes the identity number of the supplier, serial B, the order details, and is sent to the supplier terminal. The supplier terminal receives the first data pack stores the order details and serial B. The second data pack includes serial B, the encounter number the identity number of the supplier and is sent to the encounter database. The encounter database receives the second data pack from the transaction database looks up the encounter number in both the data pack and the encounter database to access the associated identity number to create a third data pack. The third data pack includes the identity number of the ordering party and the supplier's identity number which the encounter number sends to the enrollment database. The enrollment database uses the third data pack to generate a fourth data pack and a fifth data pack. The serial number assigned by the transmission server to encrypt the fourth data pack prior to it's transmission to the supplier terminal is used in the body of both the third and fourth data packs and is referred to herein as serial A. The fourth data pack that is sent to the supplier terminal includes the supplier's identity number the identity of the ordering party, and serial A. The fifth data pack including the identity number of the ordering party, serial A and the supplier's identity number is sent from the enrollment database to the encounter database.

The enrollment database upon receipt of the third data pack sends serial A and the associated identity number to the encounter database in a fifth data pack where it is matched by identity number to the serial B to create the first rule data set.

The first rule data set contains both serial A and B that match the order to the identity information. When the supplier's terminal receives and stores the fourth data pack it initiates an inquiry to the encounter server. The inquiry data pack contains the supplier's identity number and serial A that it obtained in the fourth data pack. When the encounter server receives the inquiry from the supplier it looks for the first data set that contains serial A referenced in the inquiry and then sends the matching data set to the supplier terminal in a sixth data pack. The supplier opens the data set combines the order records and the identity records that match the data set serial numbers and processes the order.

When the order is processed the supplier sends the order details as processed and serial B to the transaction data server. The transaction data server finds the order number in the records by matching the serial B numbers and updates the order status to show that it has been processed as of that date. The transaction data server communicates per it's original instructions that the order has been processed as of the recorded date to either or both of the first access terminal at the establishment or the second access terminal at the customers location.

In a more specific embodiment of the invention, the identity includes a patient name. The first access terminal includes a computer terminal. The second access terminal includes a physician computer terminal. The order includes a medication prescription. The supplier terminal includes a pharmacy computer terminal.

In one embodiment of the invention, a government database receives records and searches the order for conducting research and creating an early warning system.

The invention is also incorporated into the method of inputting an identity into a first access terminal. The identity is conveyed to an enrollment database for verifying enrollment of the identity. The identity is further conveyed to an encounter database from the enrollment database for generating, storing and outputting an encounter number associated with the identity. The encounter number is conveyed to the first access terminal from the encounter database. An order associated with the encounter number is inputted into the first access terminal. The order and the encounter number is conveyed from the first access terminal to a transaction database that records the order and the encounter number and outputs a first data pack and a second data pack. A serial number assigned by the transmission server to encrypt the first data pack prior to transmission is used in the body of the first and second data packs and is referred to as serial B. A first data pack including the identity of the supplier, the order details, and serial B is sent to the supplier terminal. The supplier terminal receives the first data pack stores the order details and serial B. A second data pack including [the primary serial number associated with the] serial B, the encounter number, and the identity of the supplier is conveyed from the transaction database to the encounter database. The encounter database receives the second data pack from the transaction database looks up the encounter number in both the second data pack and in the encounter database from when the encounter number was issued and creates a third data pack.

The third data pack includes the identity number of the ordering party the supplier's identity number and is sent from the encounter database to the enrollment database. The enrollment database uses the third data pack to generate a fourth data pack and a fifth data pack. The serial number assigned by the transmission server to encrypt the fourth data pack prior to it's transmission to the supplier terminal is used in the body of both the fourth data packs and is referred to herein as serial A. The fourth data pack includes the supplier's identity number, serial A, the identity of the ordering party and is sent to the supplier terminal. The fifth data pack including the identity number of the ordering party, serial A, and the supplier's identity number is sent from the enrollment database to the encounter database. The enrollment database uses the supplier's identity number from the fifth data pack and from the second data pack to match serial A and serial B together to create the first rule data set. When the supplier's terminal receives and stores the fourth data pack it initiates an inquiry to the encounter server. The inquiry data pack contains the supplier's identity number and serial A that it obtained in the fourth data pack. When the encounter server receives the inquiry from the supplier it looks for the first data set that contains serial A referenced in the inquiry and then sends the data set to the supplier terminal in a sixth data pack. The supplier terminal opens the sixth pack, extracts the data set serial A and serial B information that it uses to combine the order records and the identity records that match the data set serial A and serial B numbers and processes the order.

The foregoing has outlined rather broadly the more pertinent and important features of the present invention in order that the detailed description that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be made to the following detailed description taken in connection with the accompanying drawings in which.

Similar reference characters refer to similar parts throughout the several Figures of the drawings.

DETAILED DISCUSSION

Figure 1:
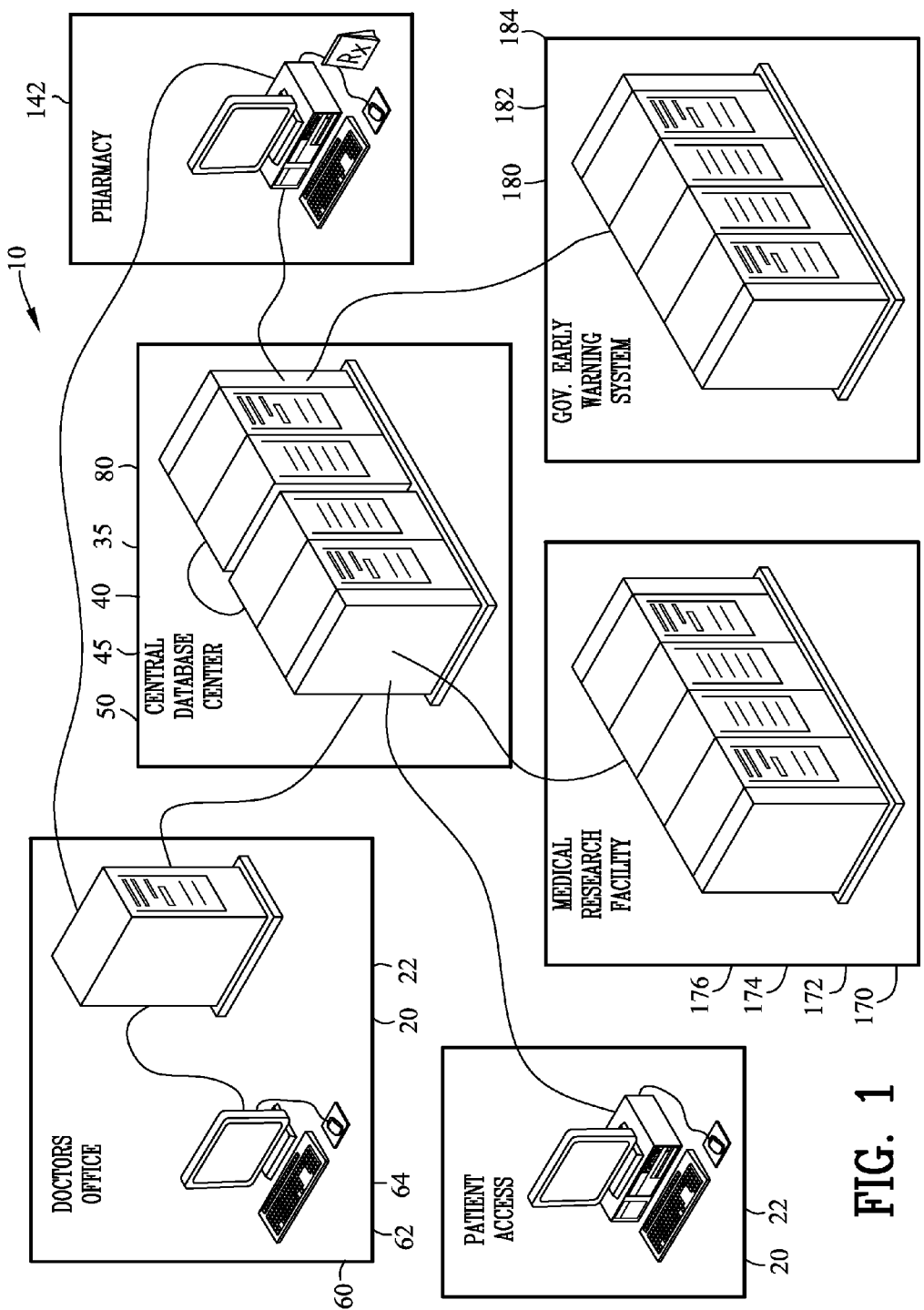
FIG. 1 is a first generalized block diagram of a network and method wherein a patient, doctor's office, Pharmacy, medical research facility and/or a governmental agency utilizes the present invention.
Figure 2:
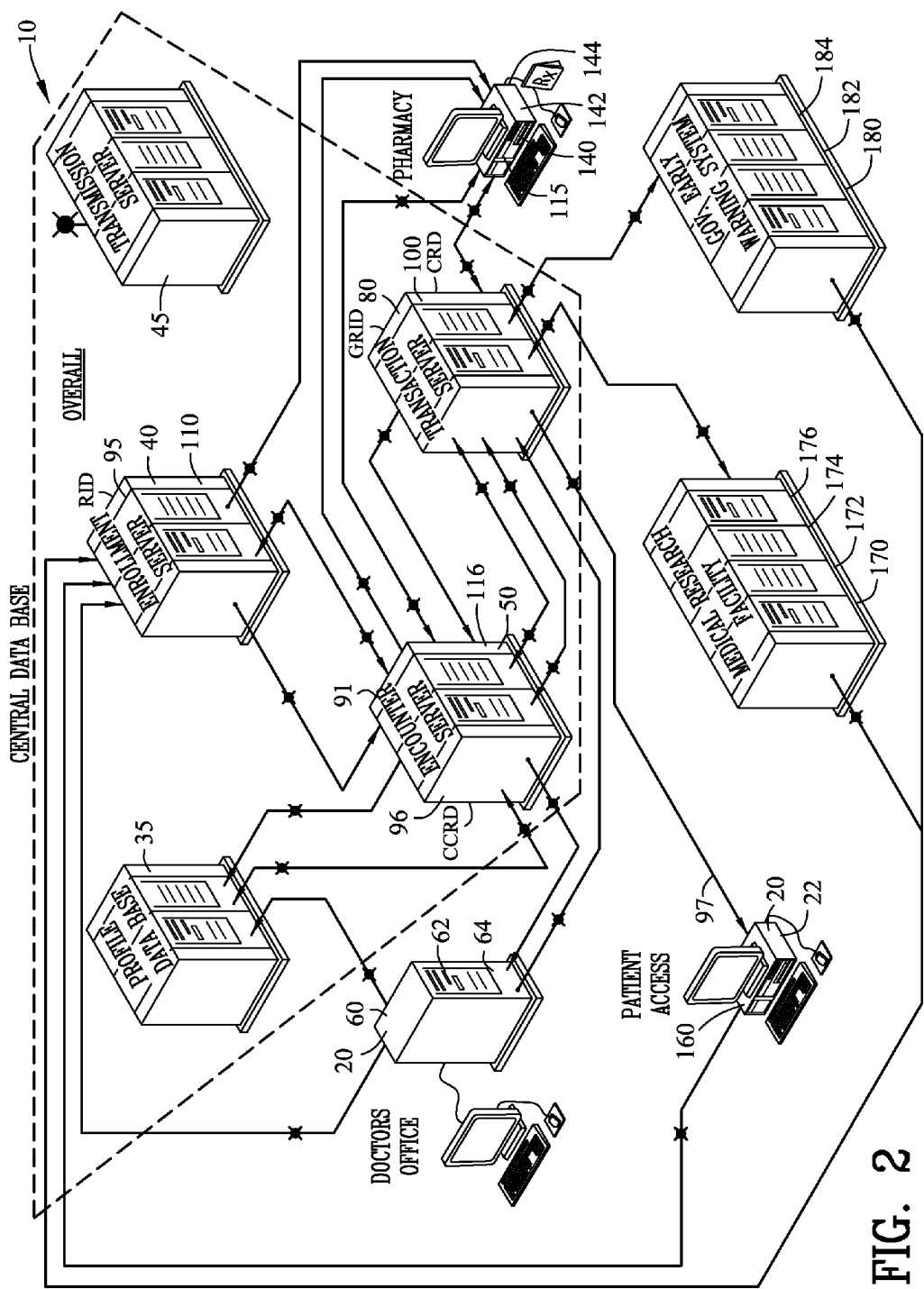
FIG. 2 is a second expanded block diagram of a network and method wherein a patient, doctor's office, medical research facility and/or a governmental agency utilizes the present invention.
Figure 2A:
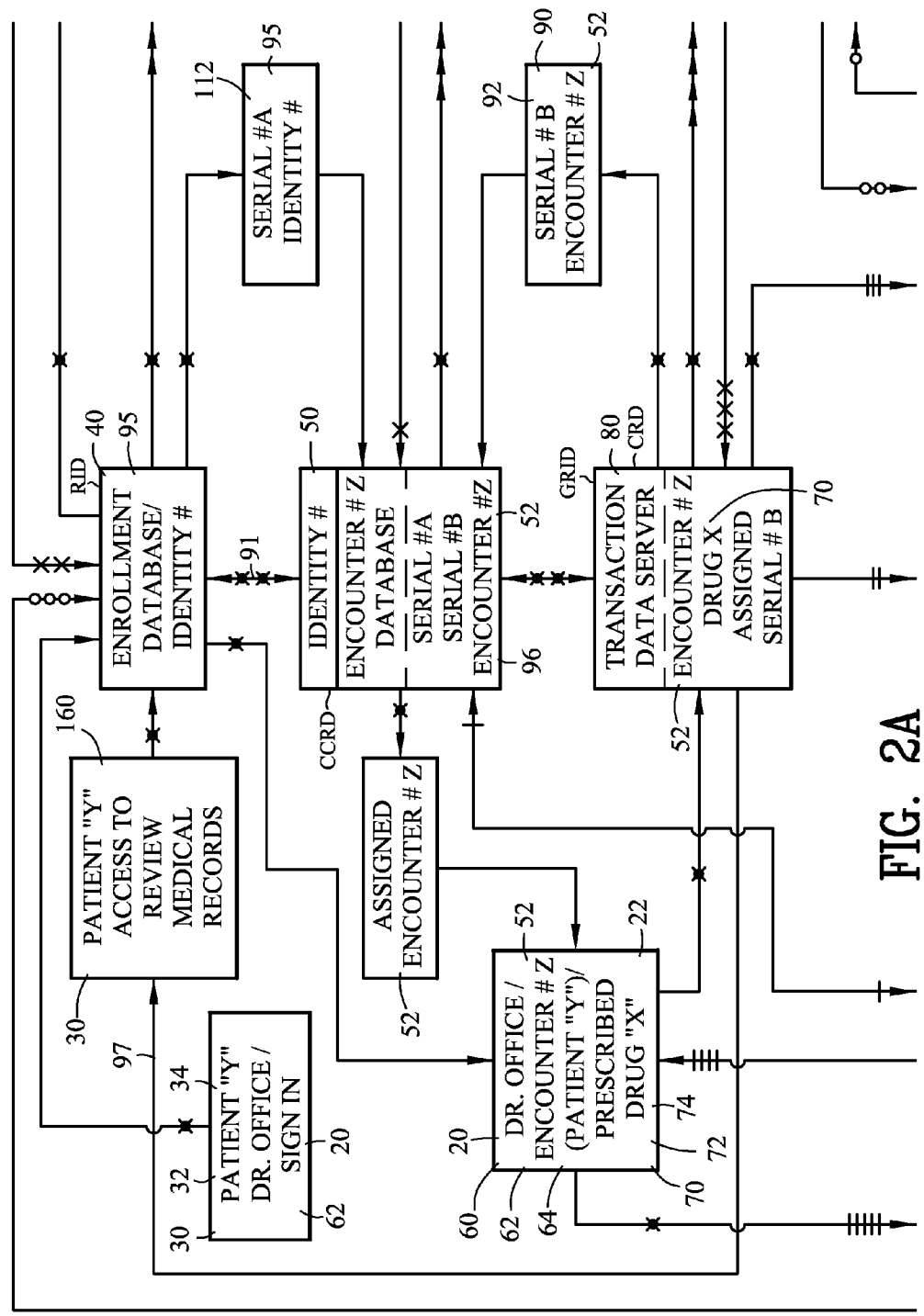
FIG. 2A is a flow diagram of FIG. 2.
Figure 2B:
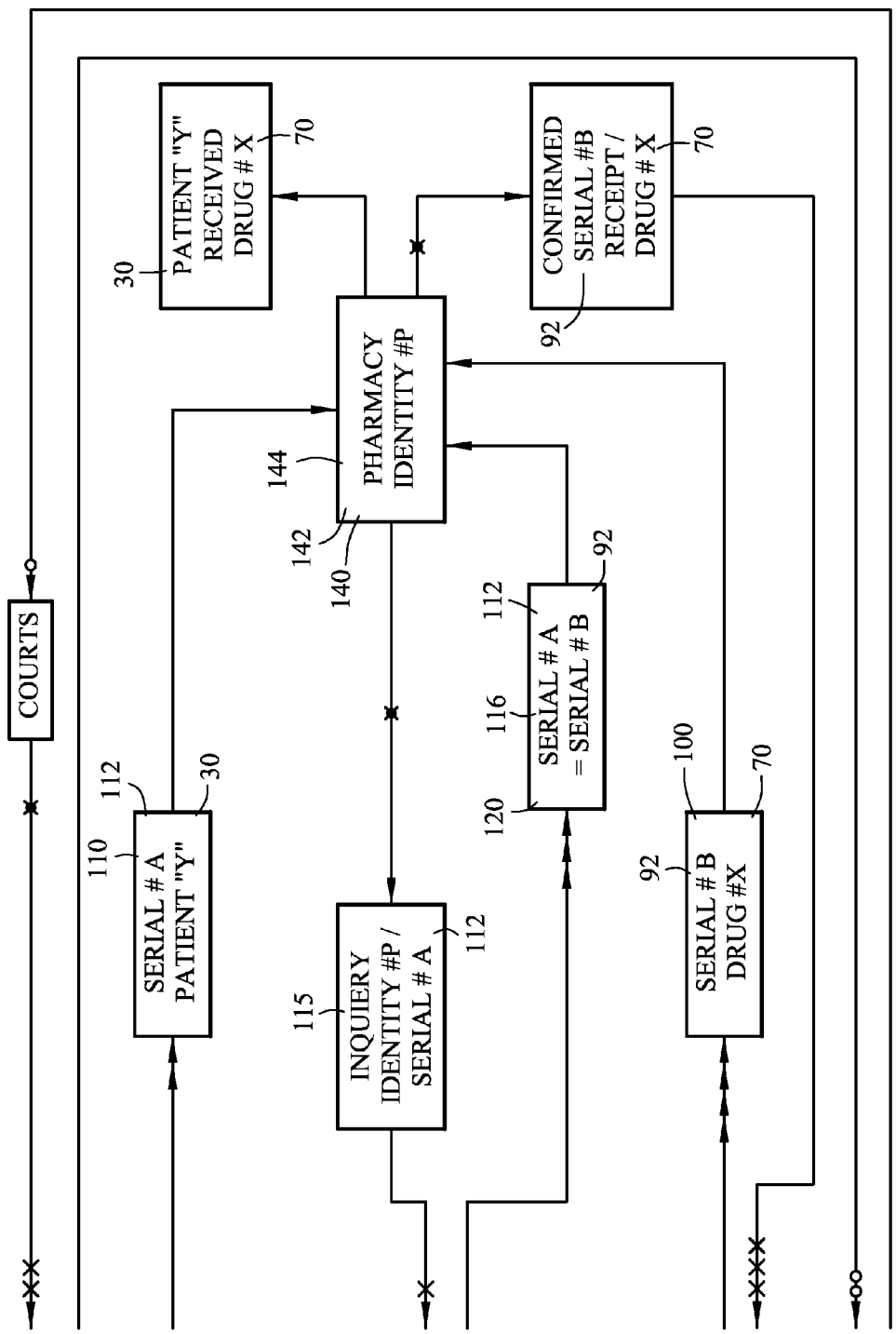
FIG. 2B is a first continued flow diagram of FIG. 2A.
Figure 2C:
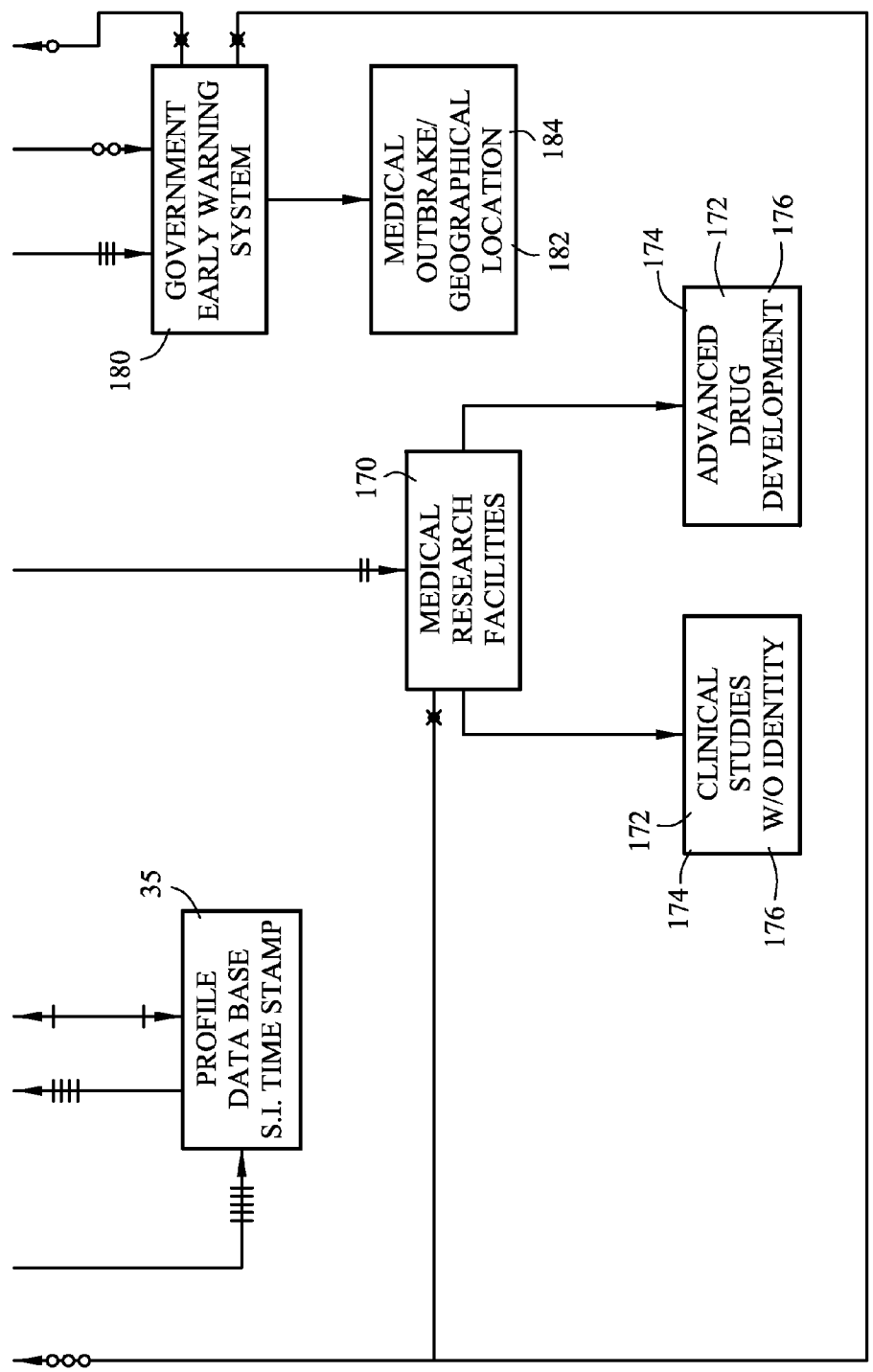
FIG. 2C is a second continued flow diagram of FIG. 2B.
Figure 3:
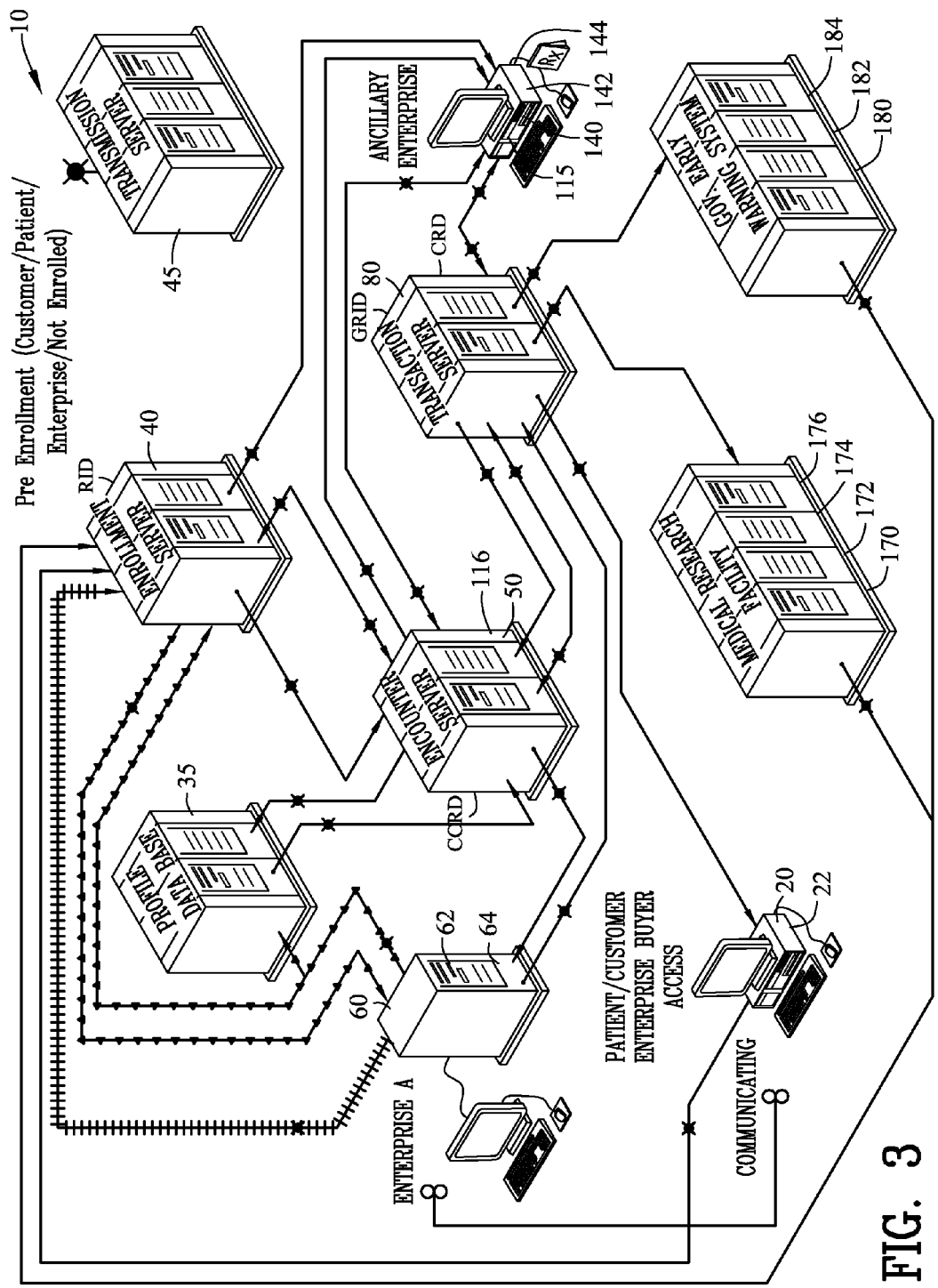
FIG. 3 is a third block diagram illustrating a pre-enrollment condition of a customer, patient, or enterprise.
Figure 4:
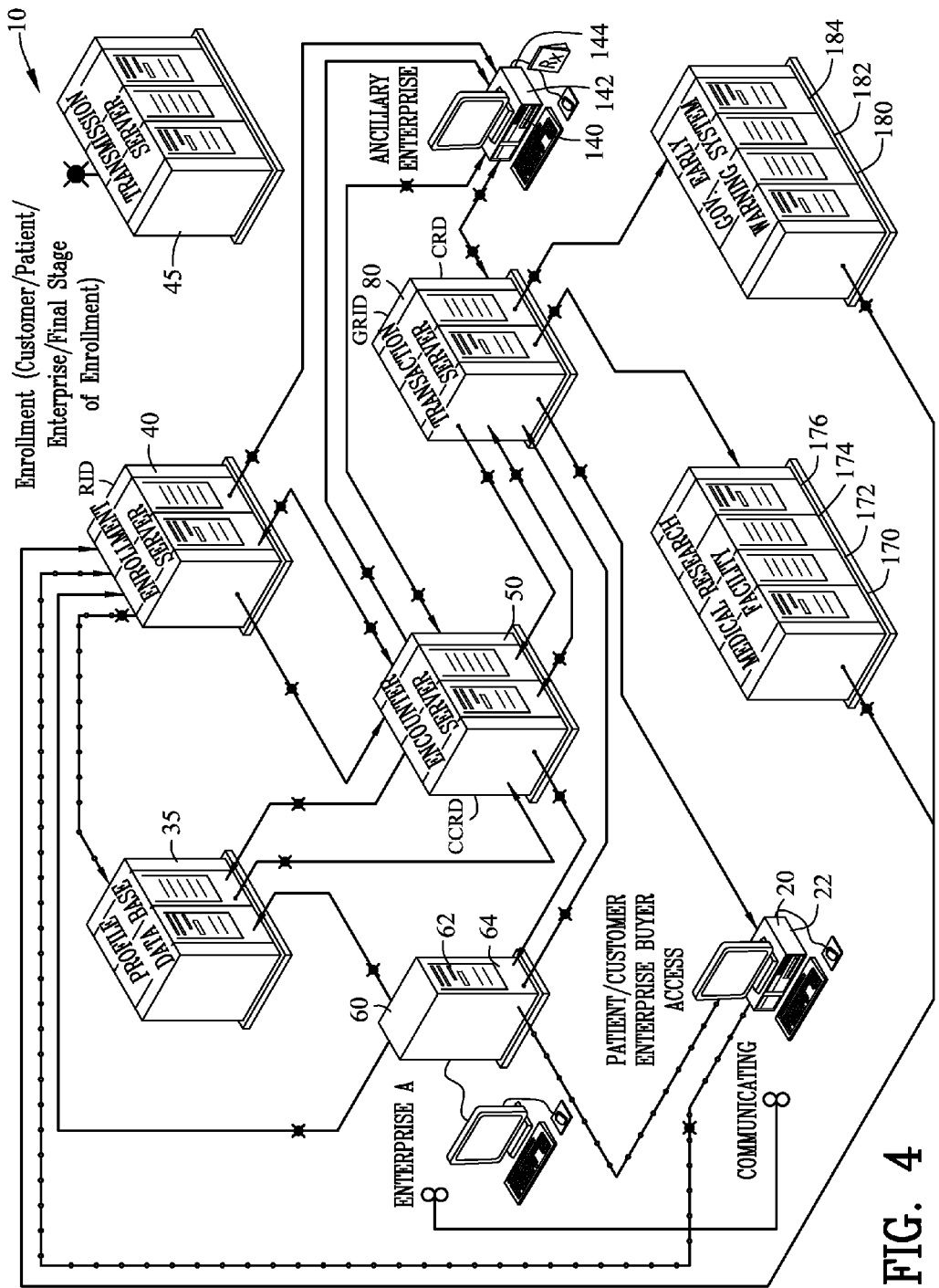
FIG. 4 is a fourth block diagram similar to FIG. 3 illustrating an enrollment condition of a customer, patient, or enterprise.
Figure 5:
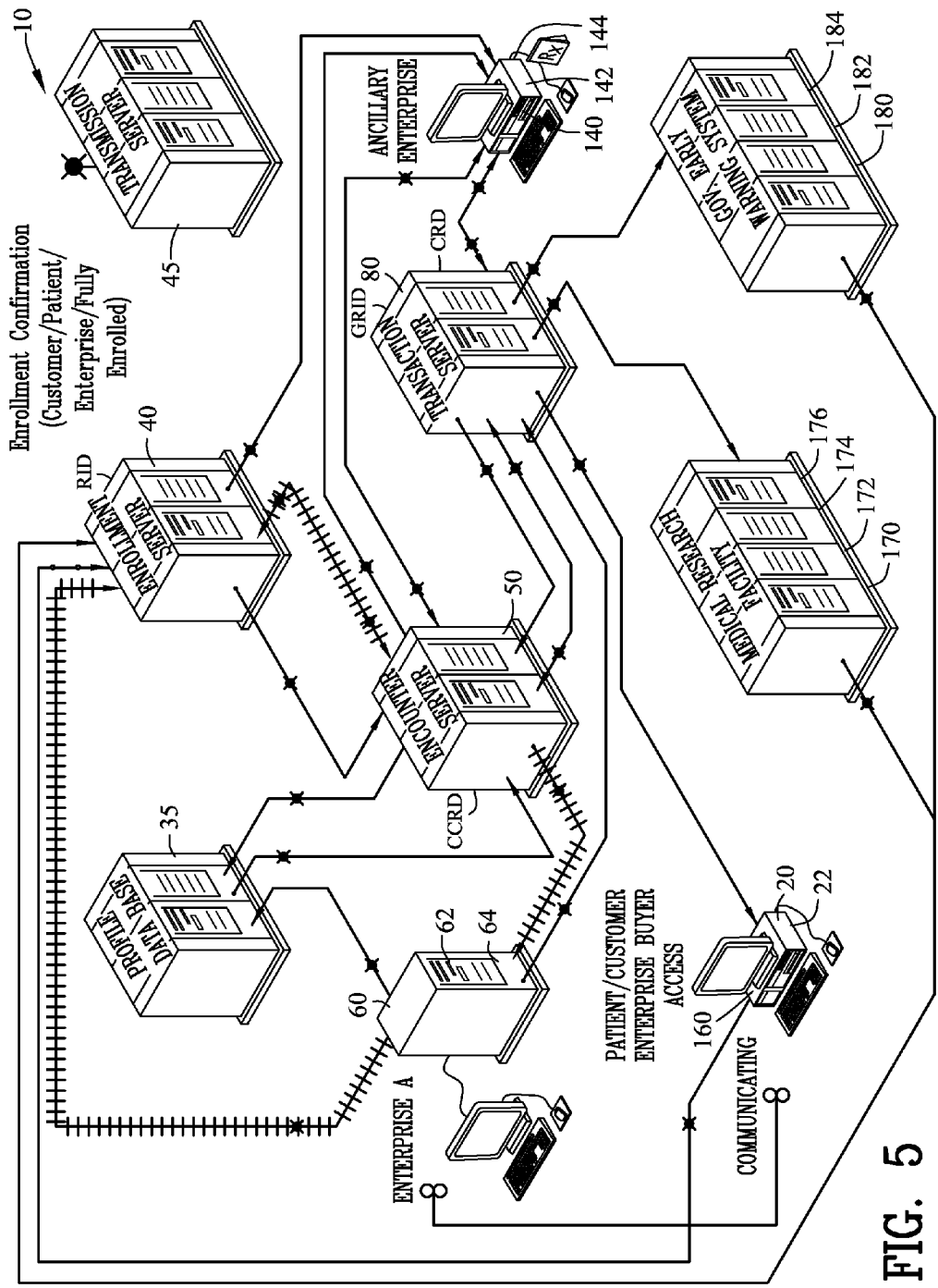
FIG. 5 is a fifth block diagram similar to FIG. 3 illustrating a confirmation of enrollment condition of a customer, patient, or enterprise.

FIGS. 1-9C illustrate an apparatus and method for a secure transaction network 10. The secure transaction network 10 comprises a first access terminal 20 or 60 for inputting an identity 30. A transmission server 45 assigning unique serial numbers for each transmission that generate a different encryption scheme for each transmission and further controls packaging and handling of data content as it is sent over a secured socket layer connection to a network destination. An enrollment database 40 receives, records, searches and outputs the identity 30 from first access terminal. An encounter database 50 receives the identity 30 from the enrollment database 40 for generating, storing and outputting an encounter number 52 associated with the identity 30. A second access terminal 60 receives the encounter number 52 from the encounter database 50 and inputs an order 70 associated with the encounter number 52. A transaction database 80 receives and records the order 70 and the encounter number 52 from the second access terminal 60 for outputting a first data pack 100 and a second data pack 90. The serial number assigned by the transmission server to encrypt the first data pack 100 prior to transmission is used in the body of both the first 100 and second data packs 90 and is referred to herein as serial B 92.

The first data pack 100 includes the identity # of the supplier 140, serial B 92, the order details 70 and is sent to the supplier terminal 142. The supplier terminal 142 receives the first data pack 100 stores the order details 70 and serial B 92. The second data pack 90 includes serial B 92, the encounter number 52, the identity number of the supplier 140 and is sent to the encounter database 50. The encounter database 50 receives the second data pack 90 from the transaction database 80 looks up the encounter number 52 in data pack 90 to access the associated Identity number 30 stored in the encounter database 50 when the encounter number 52 was generated and creates a third data pack 91. The third data pack 91 includes the identity number of the ordering party 62, the identity number of the supplier 140 and is sent to the enrollment database 40. The enrollment database 40 uses the third data pack 91 to generate a fourth data pack 110 and a fifth data pack 95. The serial number assigned by the transmission server 45 to encrypt the fourth data pack 110 prior to transmitting it to supplier terminal 142 is used in the body of both the fourth 110 and fifth data packs 95 and is referred to herein as serial A 112. The fourth data pack 110 includes the supplier's identity number 140, serial A 112, the identity of the ordering party 62 and is sent to the supplier terminal 142. The fifth data pack 95 including the identity number of the ordering party 62, serial A 112 and the supplier's identity number 140 is sent from the enrollment database 40 to the encounter database 50. The encounter database 50 uses the supplier's identity number 140 from the fifth data pack 95 and from the second data pack 90 that it received previously to matched Serial A 112 and Serial B 92 together to create the first rule data set 120. When the supplier's terminal 142 receives and stores the fourth data pack 110 it initiates an inquiry data pack 115 to the encounter server 50. The inquiry data pack 115 contains the supplier's identity number 140, and serial A 112 it obtained in the fourth data pack 110. When the encounter server 50 receives the inquiry data pack 115 from the supplier 140 it looks for the first data set 120 that contains the serial A 112 number referenced in inquiry data pack 115 and sends it to the supplier terminal 142 in the sixth data pack 116. The supplier 140 opens the sixth data pack 116, extracts the data set 120 serial A 112 and B 92 information that it uses to combine the order records 70 and the identity records 30 that match the data set 120 serial A 112 and B 92 numbers and processes the order 70. When the order 70 is processed the supplier 140 sends the order details 72 as processed and serial B 92 to the transaction data server 80. The transaction data server 80 finds the order number 70 in the records by matching the serial B 92 numbers and updates the order status to show how the order 70 was processed as of that date. The transaction data server 80 communicates per it's original instructions that the order 70 has been processed as of the recorded date to either or both of the first access terminal 60 at the establishment or the first access terminal at the customers location 20.

In one of the embodiments of the present invention, the identity 30 includes a patient name 32. The first access terminal 20 includes a computer terminal 22. The second access terminal 60 includes a physician computer terminal 62. The order 70 includes a medication prescription 72. The supplier terminal 140 includes a pharmacy computer terminal 142.

In another embodiment of the present invention, the identity 30 includes a financial account 34. The first access terminal 20 includes a computer terminal 22. The second access terminal 60 includes a financial computer terminal 64. The order 70 includes a financial transaction 74. The supplier terminal 140 includes a financial intermediary computer terminal 144 such as a bank.

As best shown in FIGS. 2-2c, 3, 4, 5, 6-6C, and 7-7C a research database 170 receives, records and searches the order 70 for conducting research 172. The research 172 may include medical research 174 without the identity 30.

Alternatively, as best shown in FIGS. 2-2c, 3, 4, 5, 6-6C, and 7-7C a government database 180 receives, records and searches the order 70 for conducting research 172 and creating an early warning system 182. The early warning system 182 may include an early warning pandemic system 184.

The present invention further includes a method for conducting a secure transaction. The method comprises the steps of inputting an identity 30 into a first access terminal. A transmission server assigning a unique serial number to each network transmission that it uses to generate a different encryption scheme for each transmission and controls how the data in each transmission is packaged and thereafter handled as it is sent over the secured socket layer connection to network destinations. The identity 30 is conveyed to an enrollment database 40 for verifying enrollment of the identity 30. The identity 30 is further conveyed to an encounter database 50 from the enrollment database 40 for generating, storing and outputting an encounter number 52 associated with the identity 30. The encounter number 52 is conveyed to a second access terminal 60 from the encounter database 50. An order 70 associated with the encounter number 52 is inputted into the second access terminal. The order 70 and the encounter number 52 are conveyed from the second access terminal 60 to a transaction database 80. The transaction database 80 receives and records the order 70 and the encounter number 52 for outputting a first data pack 100 and a second data pack 90. A serial number assigned by the transmission server 45 to encrypt the first data pack 100 prior to transmission is used in the body of the first 100 and second data packs 90 and is referred to as serial B 92. The first data pack 100 includes the identity # of the supplier 140, the order details 70 and serial B 92 that is sent to the supplier terminal 142. The supplier terminal 142 receives the first data pack 100 stores the order details 70 and serial B 92. The second data pack 90 includes serial B 92, the encounter number 52, the identity number of the supplier 140 and is sent to the encounter database 50. The encounter database 50 receives the second data pack 90 from the transaction database 80 looks up the encounter number 52 in the data pack 90 to access the associated Identity number 30 stored in the encounter database 50 when the encounter number 52 was generated. The encounter database 50 sends a third data pack 91 to the enrollment database 40. The third data pack 91 includes the identity number of the ordering party 62, the supplier's identity number 140 and is sent to the enrollment database 40. The enrollment database 40 uses the third data pack 91 to generate a fourth data pack 110 and a fifth data pack 95. The serial number assigned by the transmission server 45 to encrypt the fourth data pack 110 prior to transmitting it to supplier terminal 142 is used in the body of both the fourth 110 and fifth data packs 95 and is referred to herein as serial A 112. The fourth data pack 110 includes the supplier's identity number 140, serial A 112, the identity of the ordering party 62 and is sent to the supplier terminal 142. The fifth data pack 95 including the identity number of the ordering party 62, serial A 112 and the supplier's identity number 140 is sent from the enrollment database 40 to the encounter database 50. The encounter database 50 uses the supplier's identity number 140 from the fifth data pack 95 and from the second data pack 90 that it received previously to matched Serial A 112 and Serial B 92 together to create the first rule data set 120. When the supplier's terminal 142 receives and stores the fourth data pack 110 it initiates an inquiry data pack 115 to the encounter server 50. The inquiry data pack 115 contains the supplier's identity number 140, and serial A 112 it obtained in the fourth data pack 110. When the encounter server 50 receives the inquiry data pack 115 from the supplier 140 it looks for the first data set 120 that contains the serial A 112 number referenced in inquiry data pack 115 and sends it to the supplier terminal 142 in the sixth data pack 116. The supplier 140 opens the sixth data pack 116, extracts the data set 120 serial A 112 and B 92 information that it uses to combine the order records 70 and the identity records 30 that match the data set 120 serial A 112 and B 92 numbers and processes the order 70. When the order 70 is processed the supplier 140 sends the order details 72 as processed and serial B 92 to the transaction data server 80. The transaction data server 80 finds the order number 70 in the records by matching the serial B 92 numbers and updates the order status to show how the order 70 was processed as of that date. The transaction data server 80 communicates per it's original instructions that the order 70 has been processed as of the recorded date to either or both of the first access terminal 60 at the establishment or the first access terminal at the customers location 20.

A further step includes outputting an early warning notice 184 from the enrollment database 40 to a government database 180.

The network comprises a first access terminal located at an enrolled establishment for inputting an identity. A second access terminal located at an enrolled customers location for entering an identity. A third supplier terminal located at the establishment of an enrolled supplier to receive the secure transaction communications. An enrollment database receives, records, searches and outputs the identity of an enrolled individual from an enrolled establishment. An encounter database receives the identity from the enrollment database for generating, storing and outputting an encounter number associated with the identity. The first access terminal in the enrolled establishment receives the encounter number from the encounter database and assigns it to a transaction order that is sent to the transaction data server. A transaction database receives and records the order and the encounter number from the first access terminal for outputting a first data pack and a second data pack. A serial number assigned by the transmission server 45 to encrypt the first data pack 100 prior to transmission is used in the body of the first 100 and second data packs 90 and is referred to as serial B 92. The first data pack 100 includes the identity # of the supplier 140, the order details 70 and serial B 92 that is sent to the supplier terminal 142. The supplier terminal 142 receives the first data pack 100 stores the order details 70 and serial B 92. The second data pack 90 includes serial B 92, the encounter number 52, the identity number of the supplier 140 and is sent to the encounter database 50. The encounter database 50 receives the second data pack 90 from the transaction database 80 looks up the encounter number 52 in the data pack 90 to access the associated Identity number 30 stored in the encounter database 50 when the encounter number 52 was generated. The encounter database 50 sends a third data pack 91 to the enrollment database 40. The third data pack 91 includes the identity number of the ordering party 62, the supplier's identity number 140 and is sent to the enrollment database 40. The enrollment database 40 uses the third data pack 91 to generate a fourth data pack 110 and a fifth data pack 95. The serial number assigned by the transmission server 45 to encrypt the fourth data pack 110 prior to transmitting it to supplier terminal 142 is used in the body of both the fourth 110 and fifth data packs 95 and is referred to herein as serial A 112. The fourth data pack 110 includes the supplier's identity number 140, serial A 112, the identity of the ordering party 62 and is sent to the supplier terminal 142. The fifth data pack 95 including the identity number of the ordering party 62, serial A 112 and the supplier's identity number 140 is sent from the enrollment database 40 to the encounter database 50. The encounter database 50 uses the supplier's identity number 140 from the fifth data pack 95 and from the second data pack 90 that it received previously to matched Serial A 112 and Serial B 92 together to create the first rule data set 120. When the supplier's terminal 142 receives and stores the fourth data pack 110 it initiates an inquiry data pack 115 to the encounter server 50. The inquiry data pack 115 contains the supplier's identity number 140, and serial A 112 it obtained in the fourth data pack 110. When the encounter server 50 receives the inquiry data pack 115 from the supplier 140 it looks for the first data set 120 that contains the serial A 112 number referenced in inquiry data pack 115 and sends it to the supplier terminal 142 in the sixth data pack 116. The supplier 140 opens the sixth data pack 116, extracts the data set 120 serial A 112 and B 92 information that it uses to combine the order records 70 and the identity records 30 that match the data set 120 serial A 112 and B 92 numbers and processes the order 70. When the order 70 is processed the supplier 140 sends the order details 72 as processed and serial B 92 to the transaction data server 80. The transaction data server 80 finds the order number 70 in the records by matching the serial B 92 numbers and updates the order status to show how the order 70 was processed as of that date. The transaction data server 80 communicates per it's original instructions that the order 70 has been processed as of the recorded date to either or both of the first access terminal 60 at the establishment or the first access terminal at the customers location 20.

The customer access terminal can be utilized to contact the enrollment server to authenticate the customer and allow them access to their transaction information. This access will allow them to determine the status of pending orders, to review or copy any past orders or to access the inventions communication features to create new orders or initiate new contacts and or communications.

In an other embodiment of the invention the order data as depicted previously is replace instead with communication data creating an improved method and apparatus for a secure data communication network. The invention has been designed to incorporate all current data forms of commercially acceptable communication and contact not limited to voice, data, video, voice mail, email, fax, barcode, snail mail, deliveries, website contacts, an in person meetings.

In one embodiment of the invention, a government early warning system is created by searching all orders for specific events that trigger inquiries that produce reports that contain order information as well as profile information without revealing identity information. This information is gathered and reported to the agencies of the government within moments of the recording of the actual order. In most cases the customer who's identity has not been revealed has not had the time to leave the premises of the establishment where they initiated the order.

The secure transaction network 10 may further comprises a transmission server 45 assigning unique serial numbers for each transmission that generate different encryption schemes and further controls the packaging and handling of data content as it is sent over a secured socket layer connection to a known network destination. A first access terminal 60 located within an enrolled business establishment for inputting an identity 30. An enrollment database 40 receives, records, searches and outputs the identity 30. An encounter database 50 receives the identity 30 from the enrollment database 40 for generating, storing and outputting an encounter number 52 associated with the identity 30. Terminal 60 receives the encounter number 52 from the encounter database 50 and inputs an order 70 associated with the encounter number 52. A transaction database 80 receives and records the order 70 and the encounter number 52 from Terminal 60 for outputting a first data pack 100 and a second data pack 90. A serial number assigned by the transmission server 45 to encrypt the first data pack 100 prior to transmission is used in the body of the first 100 and second data packs 90 and is referred to as serial B 92. The first data pack 100 includes the identity # of the supplier 140, the order details 70 and serial B 92 that is sent to the supplier terminal 142. The supplier terminal 142 receives the first data pack 100 stores the order details 70 and serial B 92. The second data pack 90 includes serial B 92, the encounter number 52, the identity number of the supplier 140 and is sent to the encounter database 50. The encounter database 50 receives the second data pack 90 from the transaction database 80 looks up the encounter number 52 in the data pack 90 to access the associated Identity number 30 stored in the encounter database 50 when the encounter number 52 was generated. The encounter database 50 sends a third data pack 91 to the enrollment database 40. The third data pack 91 includes the identity number of the ordering party 62, the supplier's identity number 140 and is sent to the enrollment database 40. The enrollment database 40 uses the third data pack 91 to generate a fourth data pack 110 and a fifth data pack 95. The serial number assigned by the transmission server 45 to encrypt the fourth data pack 110 prior to transmitting it to supplier terminal 142 is used in the body of both the fourth 110 and fifth data packs 95 and is referred to herein as serial A 112. The fourth data pack 110 includes the supplier's identity number 140, serial A 112, the identity of the ordering party 62 and is sent to the supplier terminal 142. The fifth data pack 95 including the identity number of the ordering party 62, serial A 112 and the supplier's identity number 140 is sent from the enrollment database 40 to the encounter database 50. The encounter database 50 uses the supplier's identity number 140 from the fifth data pack 95 and from the second data pack 90 that it received previously to matched Serial A 112 and Serial B 92 together to create the first rule data set 120. When the supplier's terminal 142 receives and stores the fourth data pack 110 it initiates an inquiry data pack 115 to the encounter server 50. The inquiry data pack 115 contains the supplier's identity number 140, and serial A 112 it obtained in the fourth data pack 110. When the encounter server 50 receives the inquiry data pack 115 from the supplier 140 it looks for the first data set 120 that contains the serial A 112 number referenced in inquiry data pack 115 and sends it to the supplier terminal 142 in the sixth data pack 116. The supplier 140 opens the sixth data pack 116, extracts the data set 120 serial A 112 and B 92 information that it uses to combine the order records 70 and the identity records 30 that match the data set 120 serial A 112 and B 92 numbers and processes the order 70. When the order 70 is processed the supplier 140 sends the order details 72 as processed and serial B 92 to the transaction data server 80. The transaction data server 80 finds the order number 70 in the records by matching the serial B 92 numbers and updates the order status to show how the order 70 was processed as of that date. The transaction data server 80 communicates per it's original instructions that the order 70 has been processed as of the recorded date to either or both of the first access terminal 60 at the establishment or the first access terminal at the customers location 20.

In another embodiment of the present invention, the identity 30 includes a financial account 34. The second access terminal 20 includes a computer terminal 22. The first access terminal 60 includes a financial computer terminal 64. The order 70 includes a financial transaction 74. The supplier terminal 140 includes a financial intermediary computer terminal 144 such as a bank.

Figure 6:
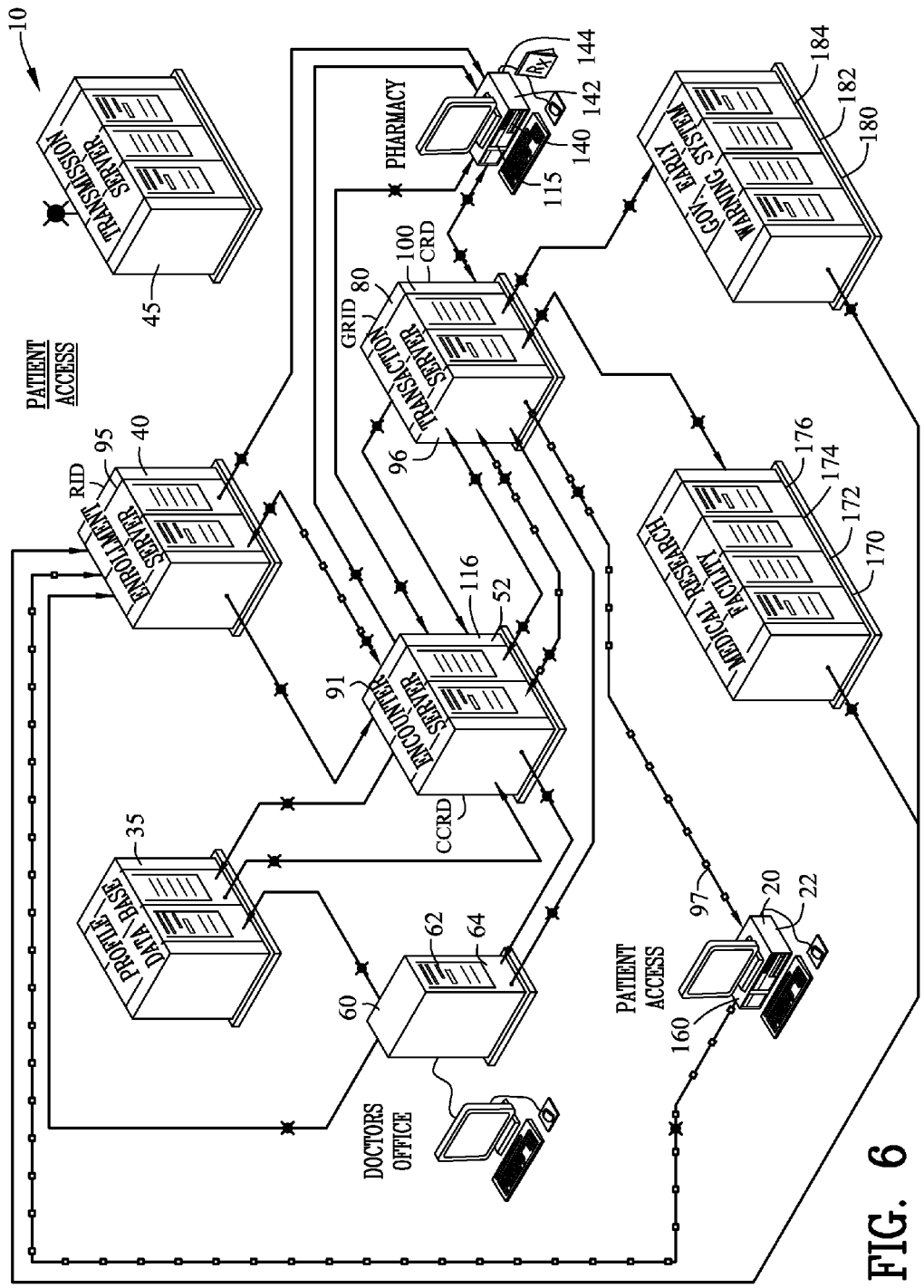
FIG. 6 is a sixth block diagram of a network and method wherein a patient is accessing the present invention.
Figure 6A:
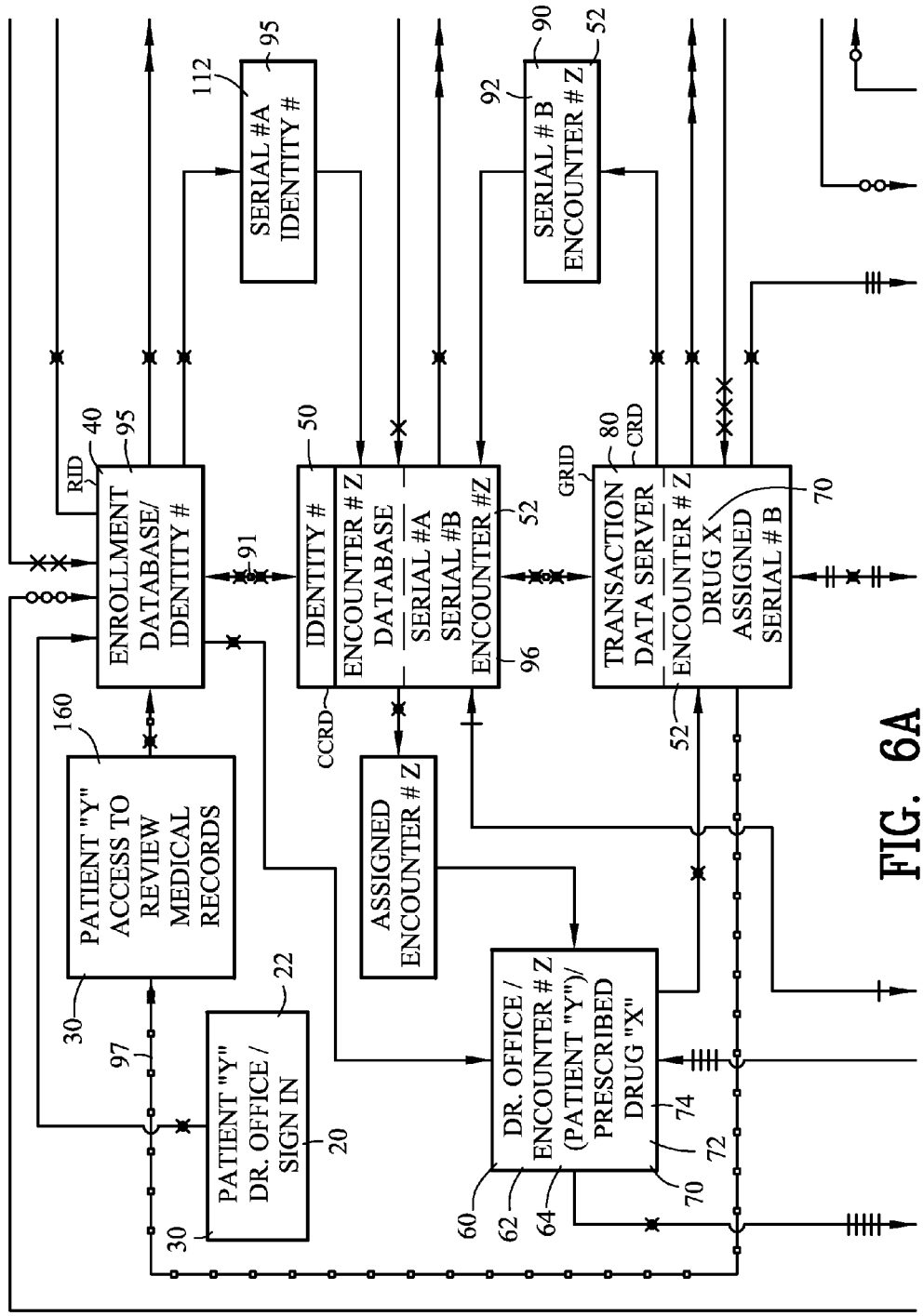
FIG. 6A is a flow diagram of FIG. 6.
Figure 6B:
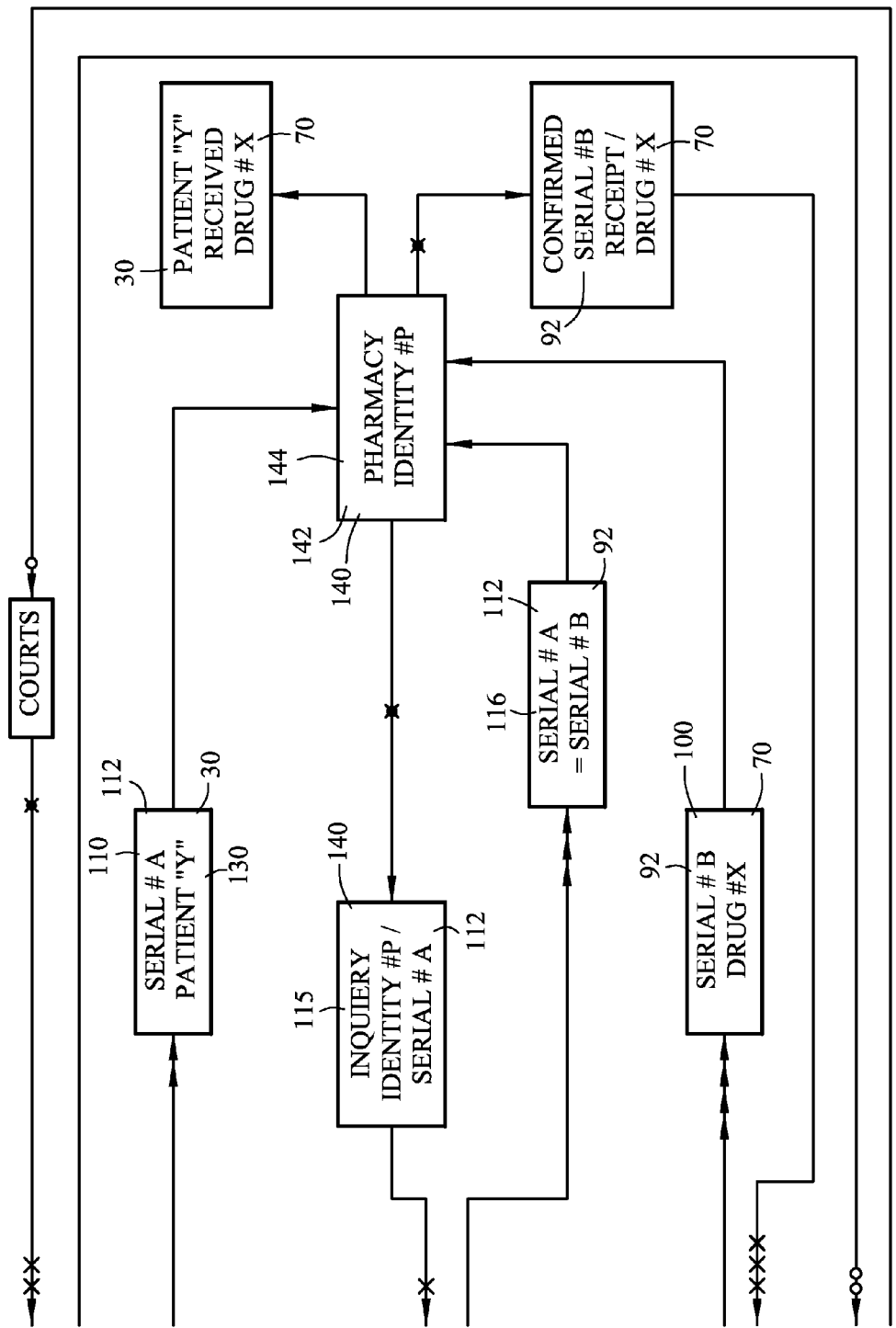
FIG. 6B is a first continued flow diagram of FIG. 6A.
Figure 6C:
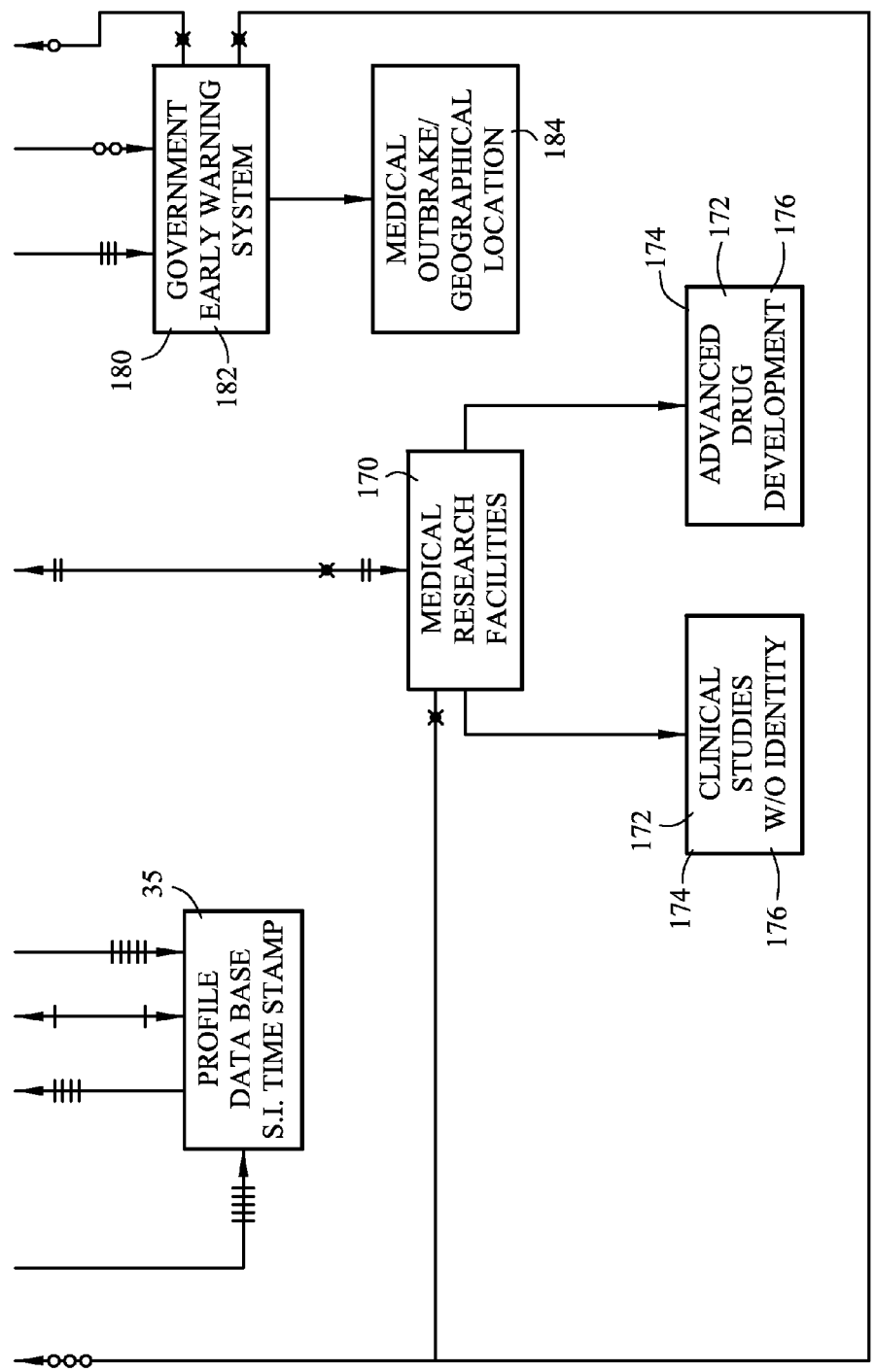
FIG. 6C is a second continued flow diagram of FIG. 6A.

As best shown in FIG. 6-6C, the second access terminal 20 includes a computer terminal 22 that inputs the identity 30 for requesting access to an identity record 160. The enrollment database 40 receives the identity 30 from the second access terminal for verifying enrollment of the identity 30. The enrollment database 40 outputs the identity record 160 request for the identity 30 to the encounter database that looks up all encounter numbers associated with identity 30 and compiles them into data pack 96 that is sent to the transaction data server. The data pack 96 contains a list of all encounter numbers associated with identity 30, the destination terminal to transmit identity 30 record request 160, but it does not contain any identity information. The transaction server assembles all records chronologically by encounter number and transmits data pack 97 to the designated destination terminal 22.

In another embodiment of the present invention the identity record request 160 initiated at terminal 22 can be directed to an identified destination terminal other than terminal 22. Patients would use this capability to send their medical records to any new doctors or hospital emergency rooms that would provide current or future medical services. In this situation the new doctor would be treated in the same way that pharmacy # P was handled in the illustration above to complete a record transmission.

Figure 7:
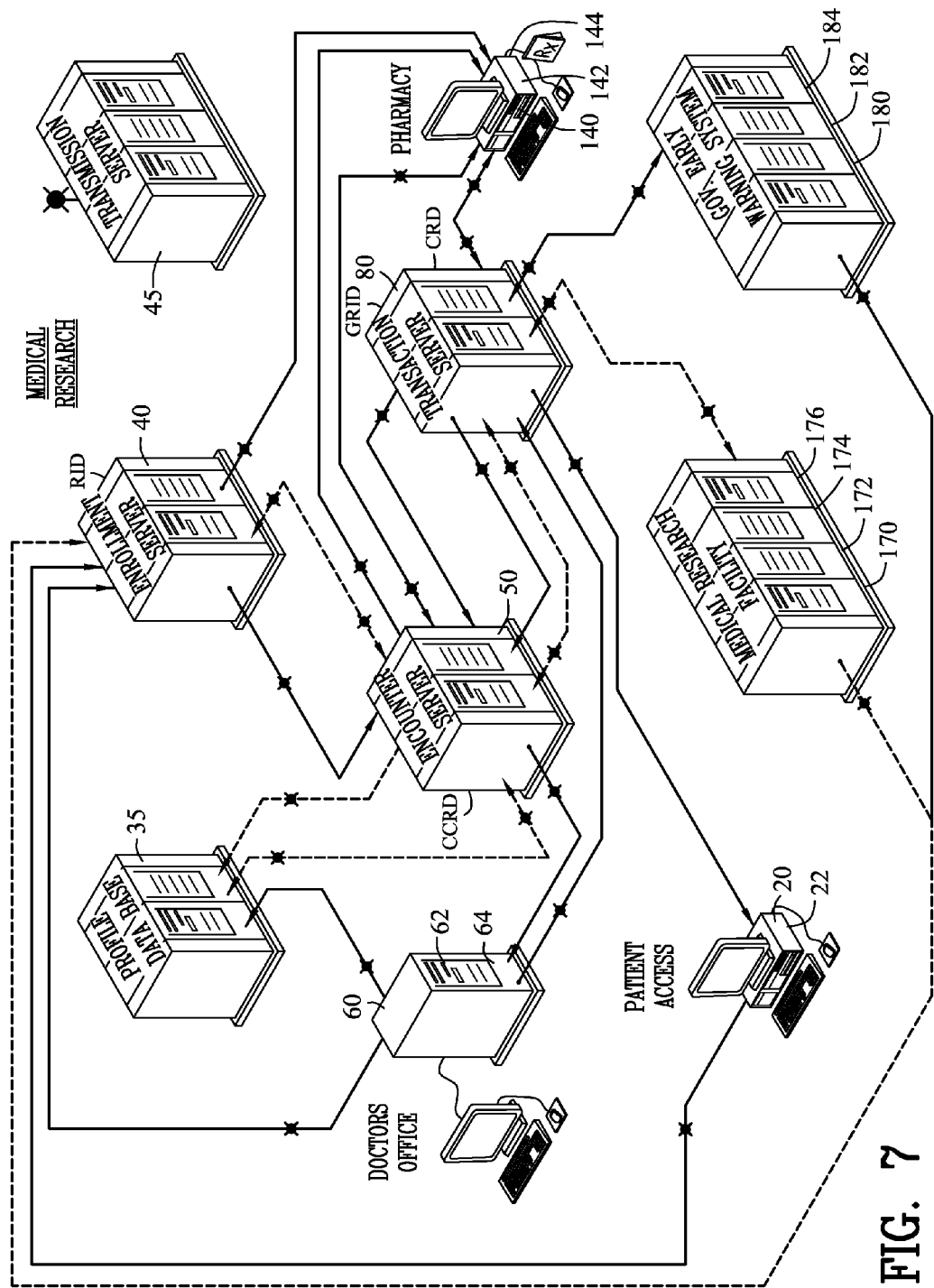
FIG. 7 is a seventh block diagram of a network and method wherein a medical research facility is accessing the present invention.
Figure 7A:
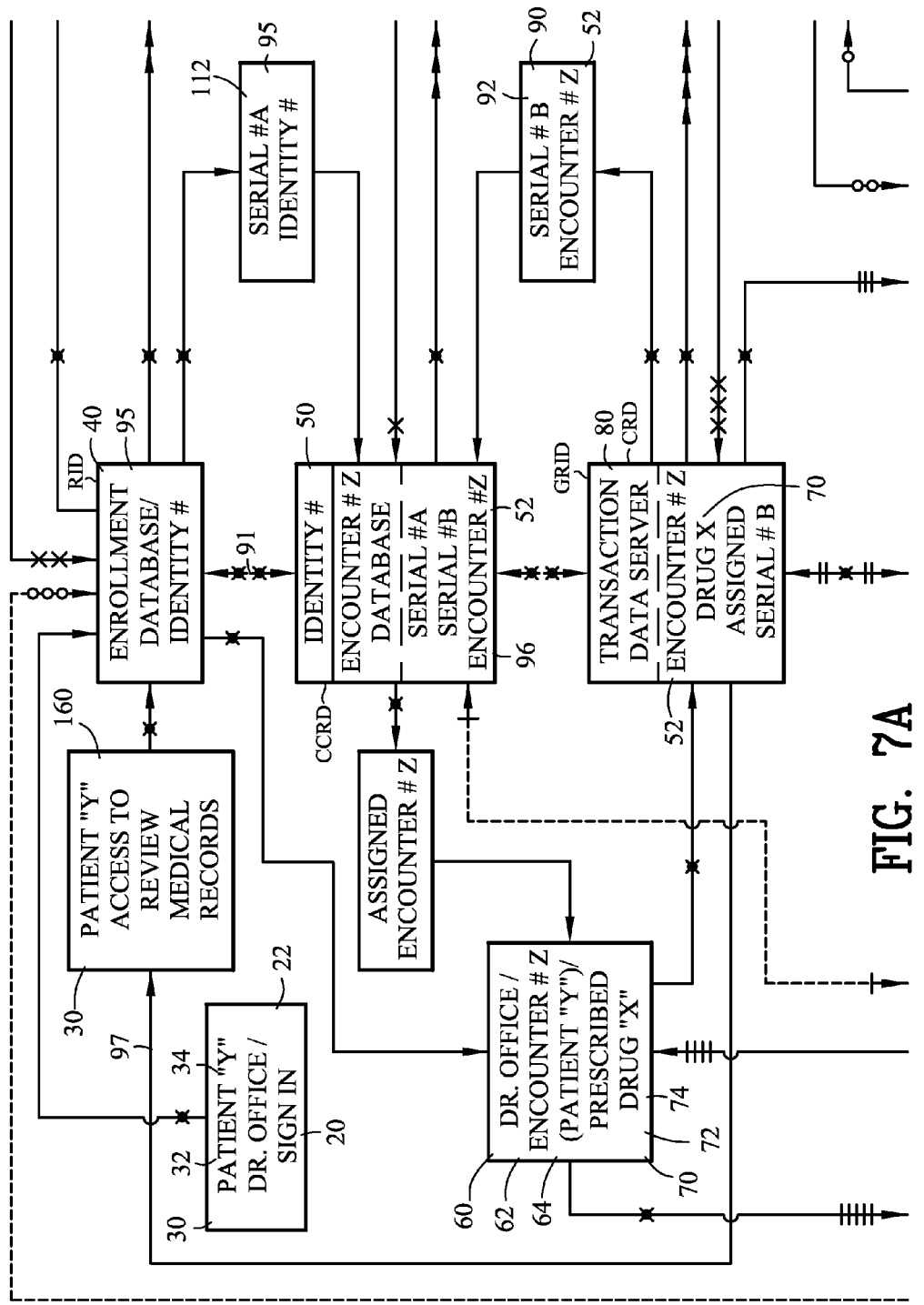
FIG. 7A is a flow diagram of FIG. 7.
Figure 7B:
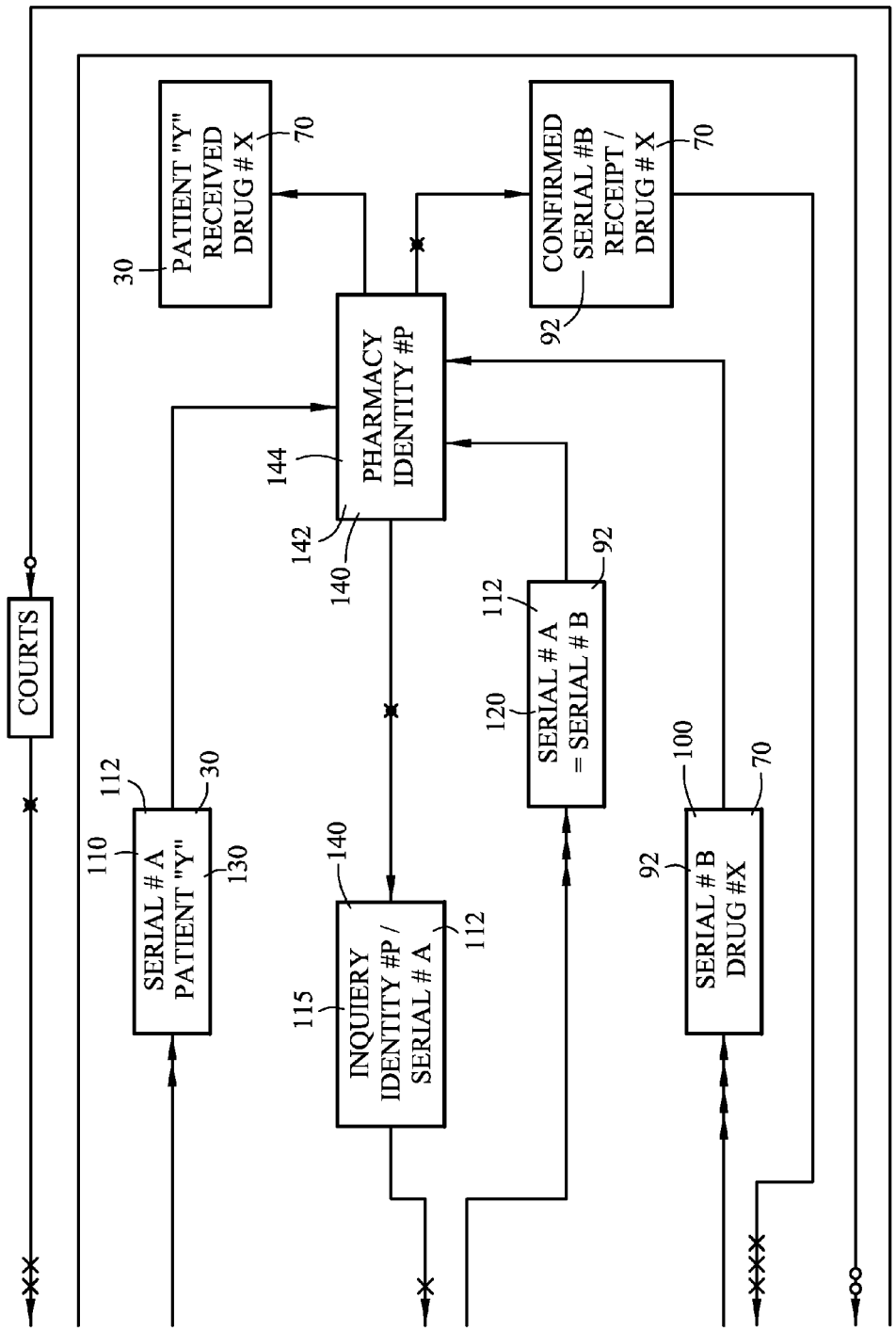
FIG. 7B is a first continued flow diagram of FIG. 7A.
Figure 7C:
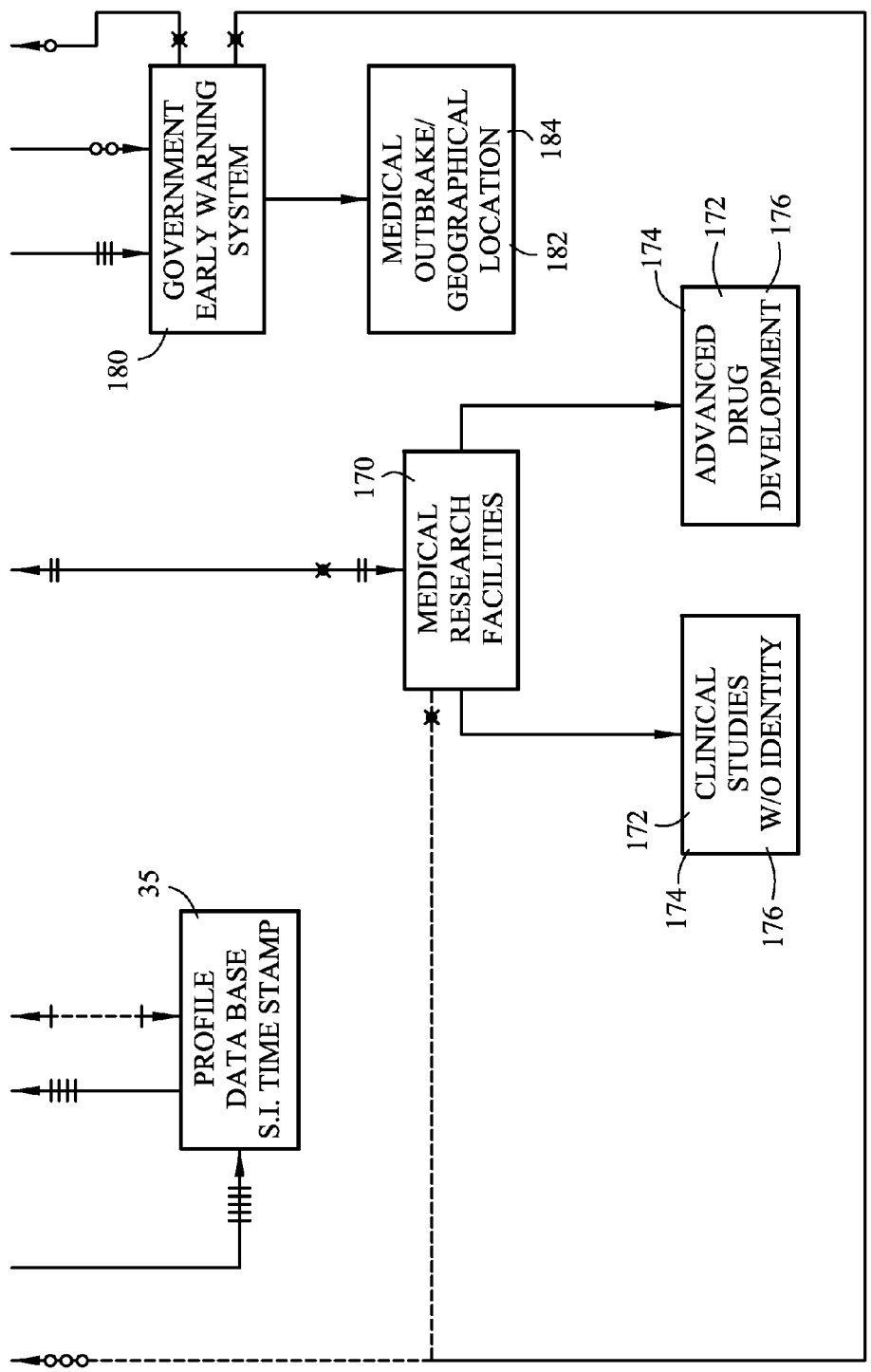
FIG. 7C is a second continued flow diagram of FIG. 7A.

As best shown in FIGS. 7-7C, a research database 170 creates a research inquiry request 172. The records request is next conveyed from the research database 170 to the enrollment database 40 for the enrollment database 40 to be authenticated and create a research inquiry data base entry. The research inquiry database or RID housed on the enrollment server assigns an inquiry number, records the title of the specific inquiry, lists the profile and transaction data to be collected, the date ranges involved, and the inquiry trigger requirements. The inquiry data collection requirements, date ranges and inquiry trigger requirements are sent to the encounter server 50 that assigns a research encounter number for this inquiry. The encounter server 50 uses the assigned research encounter number and the inquiry requirements sent from the enrollment server to compile a custom research database or CCRD to collect the information that satisfies the inquiry data collection requirements. The encounter server assembles the encounter numbers that meet the inquiry requests date range and or inquiry trigger requirements and enters the related encounter number, identity numbers and S1 information in the CCRD. The identity numbers are replaced with numbers arranged in numerical order such that all encounters that relate to the same identity are assigned the same number. The S1 information and the profile information requirements of the inquiry are collected from the CCRD and sent to the profile server 35 where the requested demographic information is assembled. The assembled profile information is sent from the profile server 35 to the encounter server 50 where it is merged into the CCRD created for that encounter inquiry. The encounter numbers and the historical record requirements of the research inquiry are extracted from the CCRD and sent to the transaction server 80. The transaction server 80 retrieves the requested historical records of the individuals included in the study from the selected encounter numbers and sends them to the encounter server 50. The encounter server 50 merges this data into the CCRD database and then sends the completed research inquiry in database form to the transaction server 80 where it is stored by the assigned inquiry encounter number. The transaction server 80 arranges the transmission of the CRD to the research facility 170 based on the specifications from the initial inquiry 172. The research facility can further manipulate the data removing or condensing instances of multiple entries for the same individual and they can do follow up inquiries that pull from the same identities used in the research inquiry database maintained in the enrollment server 40.

Figure 8:
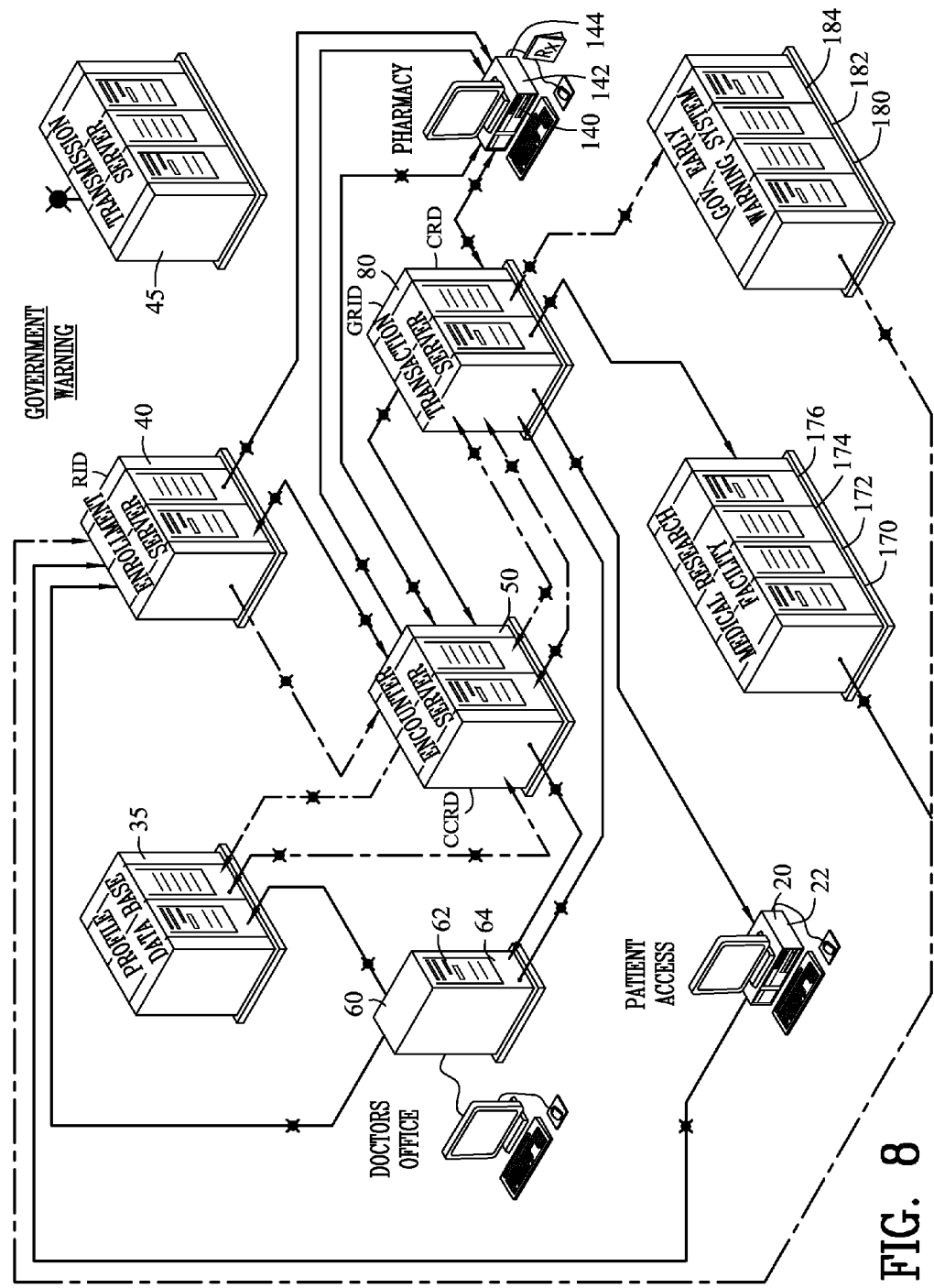
FIG. 8 is an eighth block diagram of a network and method wherein a governmental agency is utilizing the present invention.
Figure 8A:
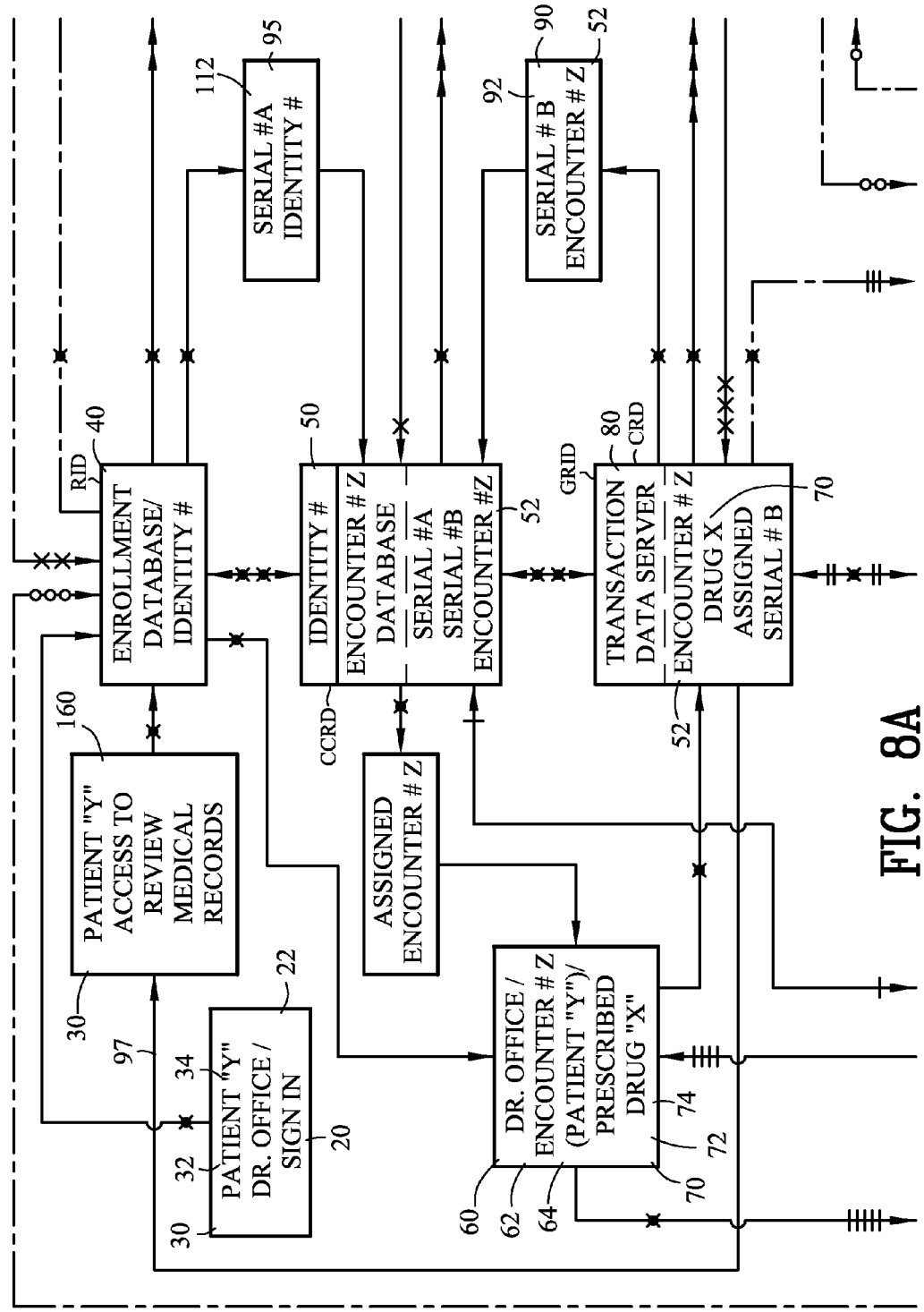
FIG. 8A is a flow diagram of FIG. 8.
Figure 8B:
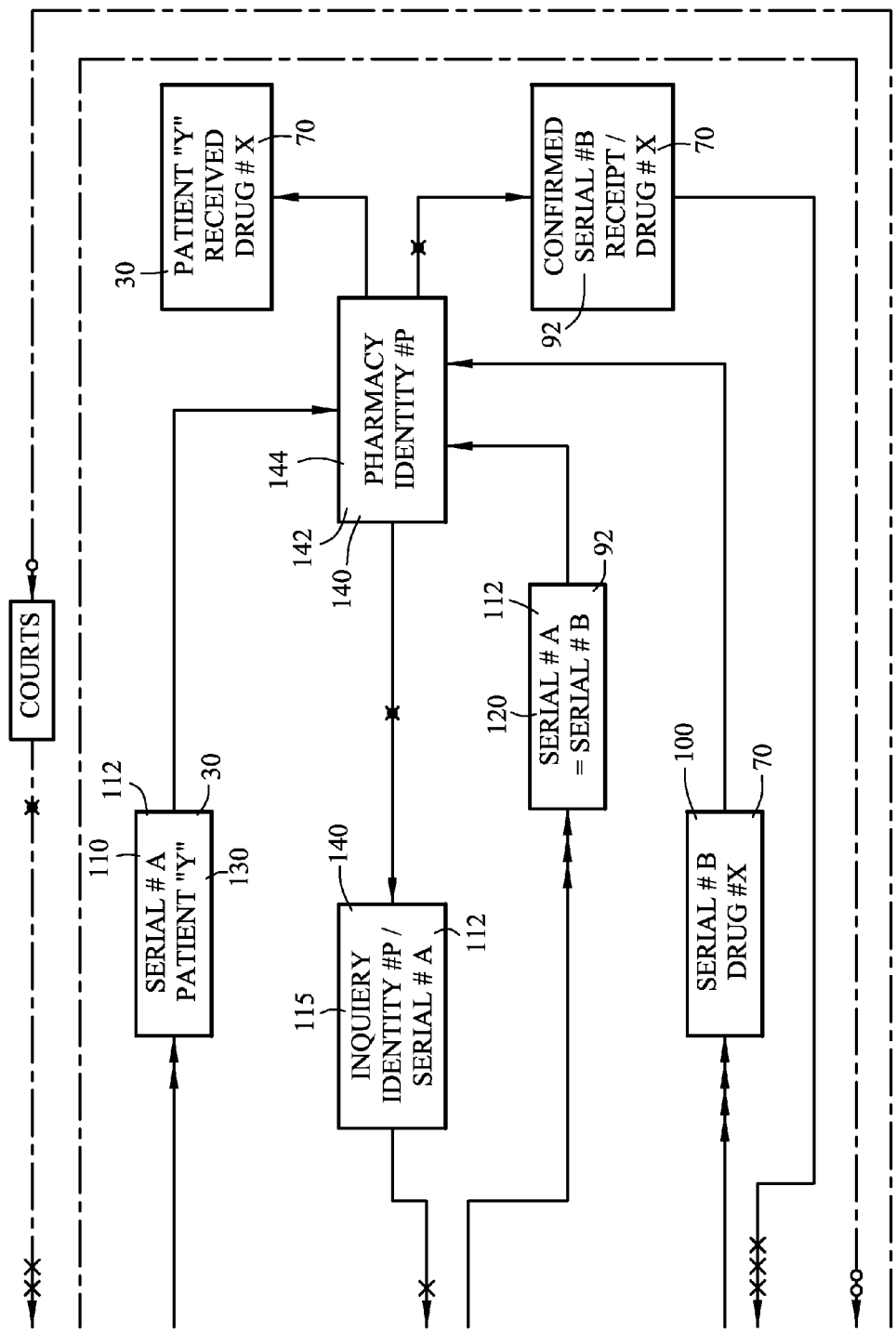
FIG. 8B is a first continued flow diagram of FIG. 8A.
Figure 8C:
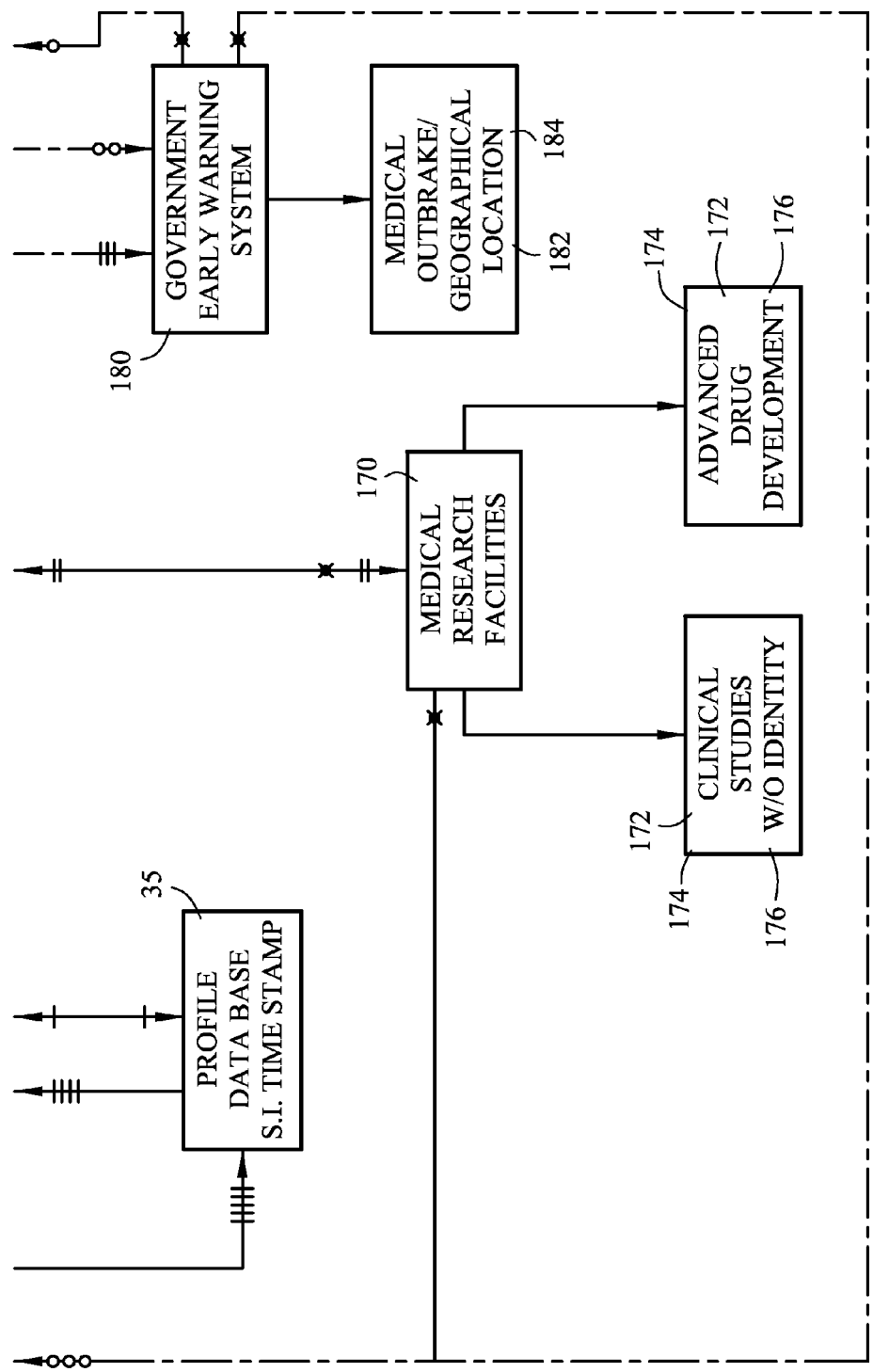
FIG. 8C is a second continued flow diagram of FIG. 8A.

Alternatively, as best shown in FIGS. 8-8C, a government database 180 creates a research inquiry 182 that identifies a transaction event or a transaction event threshold that triggers an inquiry that is part of a government early warning system 184. The inquiry identifies the transaction details and profile information to be collected and who in the government to contact. The inquiry is sent to the enrollment database 40 for authenticated and then to the encounter database 50 where the inquiry encounter number is assigned and recorded. The encounter database 50 sends the profile and transaction detail requirements, the trigger event and or threshold event information to the transaction server 80. The Transaction server 80 creates a government research inquiry database GRID to collect the trigger event and or threshold event criterion and the related transaction and profile information requirements. When encounters are added to the transaction database 80 that contain trigger events or meet trigger thresholds they are copied to the GRID located on the transaction data server 80. The encounter server 50 is sent the inquiry database entry identifier, the flagged transaction's encounter number and the inquiry encounter number. The encounter database 50 looks up the inquiry encounter number to determine the profile information to be assembled and looks up the flagged transactions encounter number to collect the S1 information related to this inquiry and if requested in the inquiry any other encounter numbers related to the identity number associated with the S1 information. The S1 information is sent to the profile server 35 where the required demographic information is extracted and sent to the encounter server 50. The encounter server logs that the profile information was received and transmits the collected profile data and any other encounter numbers if requested to the transaction database server 80 where it is entered into the GRID generating the collection of the require transaction data based on the associated encounter numbers retrieved from the encounter server 50. The transaction server 80 sends the GRID inquiry database to the government officials in the manner specified in the initial government inquiry concluding the requirements of the early warning system 184.

Figure 9:
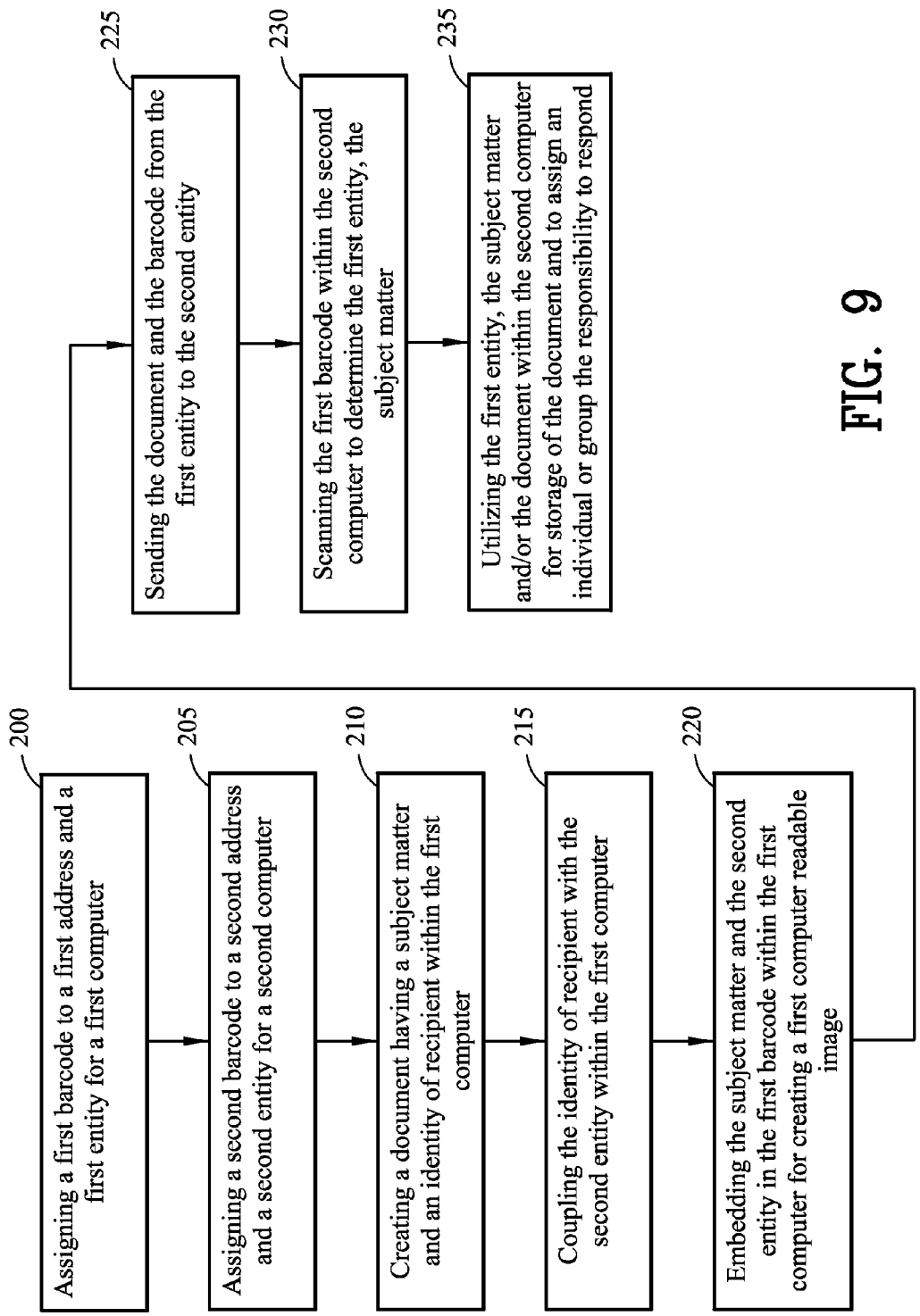
FIG. 9 is a flow diagram illustrating an apparatus and method for conducting secure communications incorporating the present invention.
Figure 10:
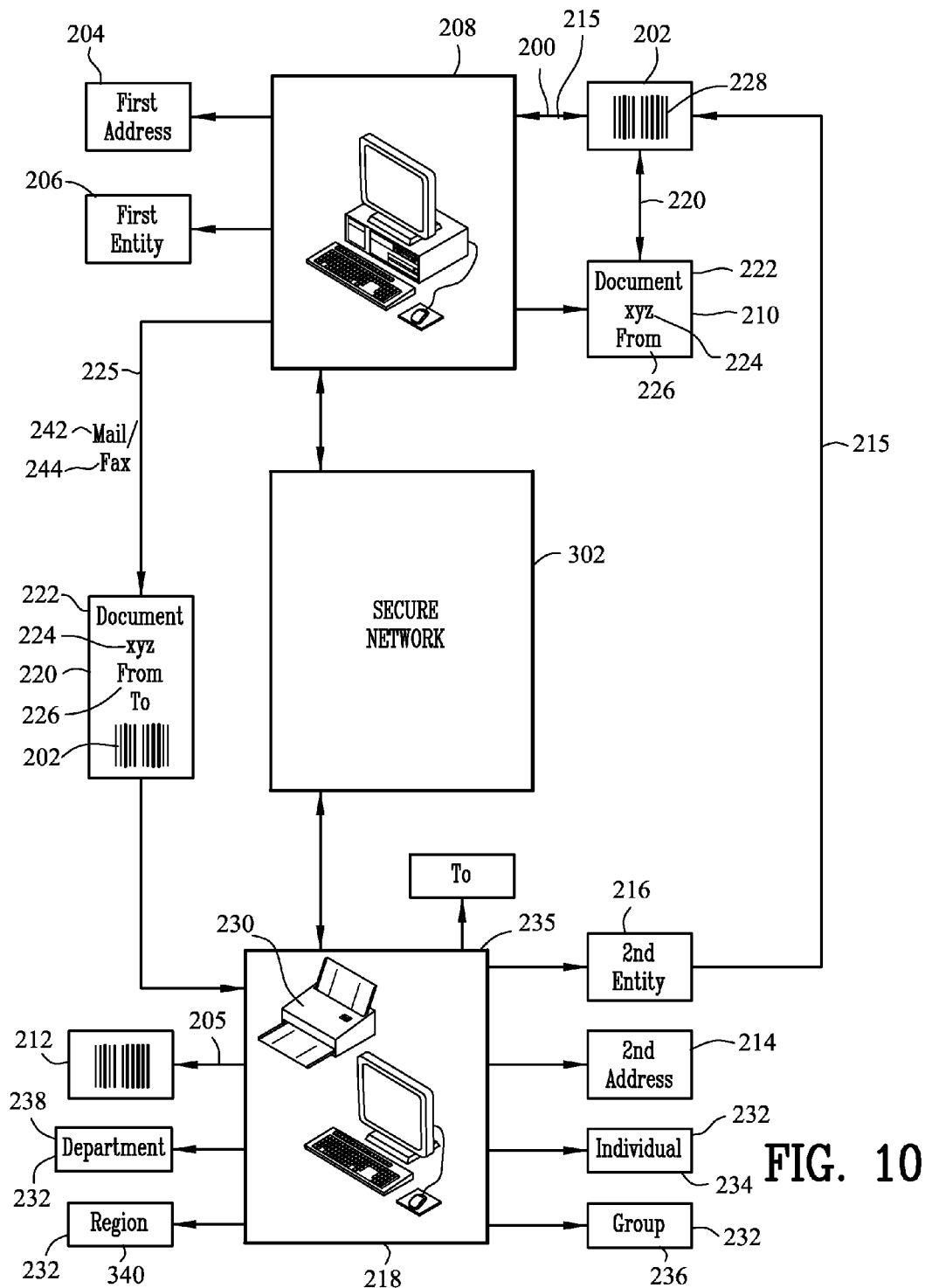
FIG. 10 is a block diagram of FIG. 9.

FIGS. 9 and 10 illustrate another embodiment of the subject invention. FIGS. 9 and 10 illustrate an apparatus and method for conducting secure communications. The apparatus and method comprising the steps of assigning 200 a first barcode 202 to a first address 204 and a first entity 206 for a first computer 208. A second barcode 212 is then assigned 205 to a second address 214 and a second entity 216 for a second computer 218. A document 222 is created 210 having a subject matter 224 and an identity of recipient 226 within the first computer 208. The identity of recipient 226 is coupled 215 with the second entity 216 within the first computer 208.

The subject matter 224 and the second entity 216 are then embedded 220 in the first barcode 202 within the first computer 208 for creating a first computer readable image 228. The document 222 and the first barcode 202 are sent 225 from the first entity 206 to the second entity 216. The act of sending 225 may include but not limited to mailing 242 through the U.S. Postal Service, or other shipping organization, facsimile 244 or other courier methods. The first barcode 202 is scanned 230 within the second computer 218 to determine the first entity 206 and the subject matter 224. The first entity 206, the subject matter 224 and/or the document 222 are utilized 235 within the second computer 218 for storage of the document 222 and/or to assign 232 an individual 234, group 236, department 238 and/or regional group 240 the responsibility to respond. The subject invention also incorporates a reminder system or an alert system wherein the assigning of a responsibility may be directed to both an individual and a department head wherein if the individual docs not respond to a requested action, the department head may be additionally notified of the lack of response by the individual.

Figure 11:
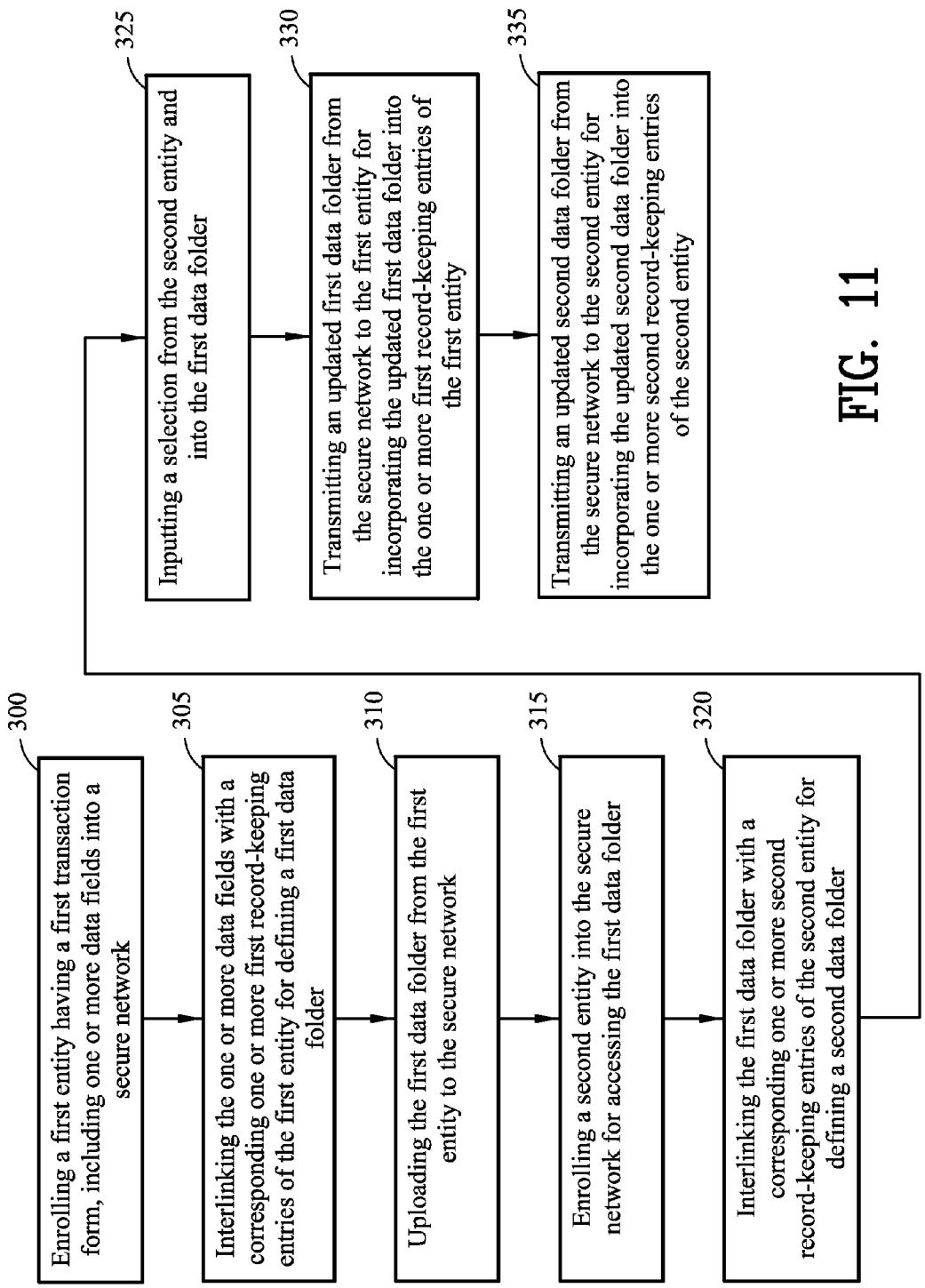
FIG. 11 is a flow diagram illustrating an apparatus and method for conducting secure business transactions incorporating the present invention.
Figure 12:
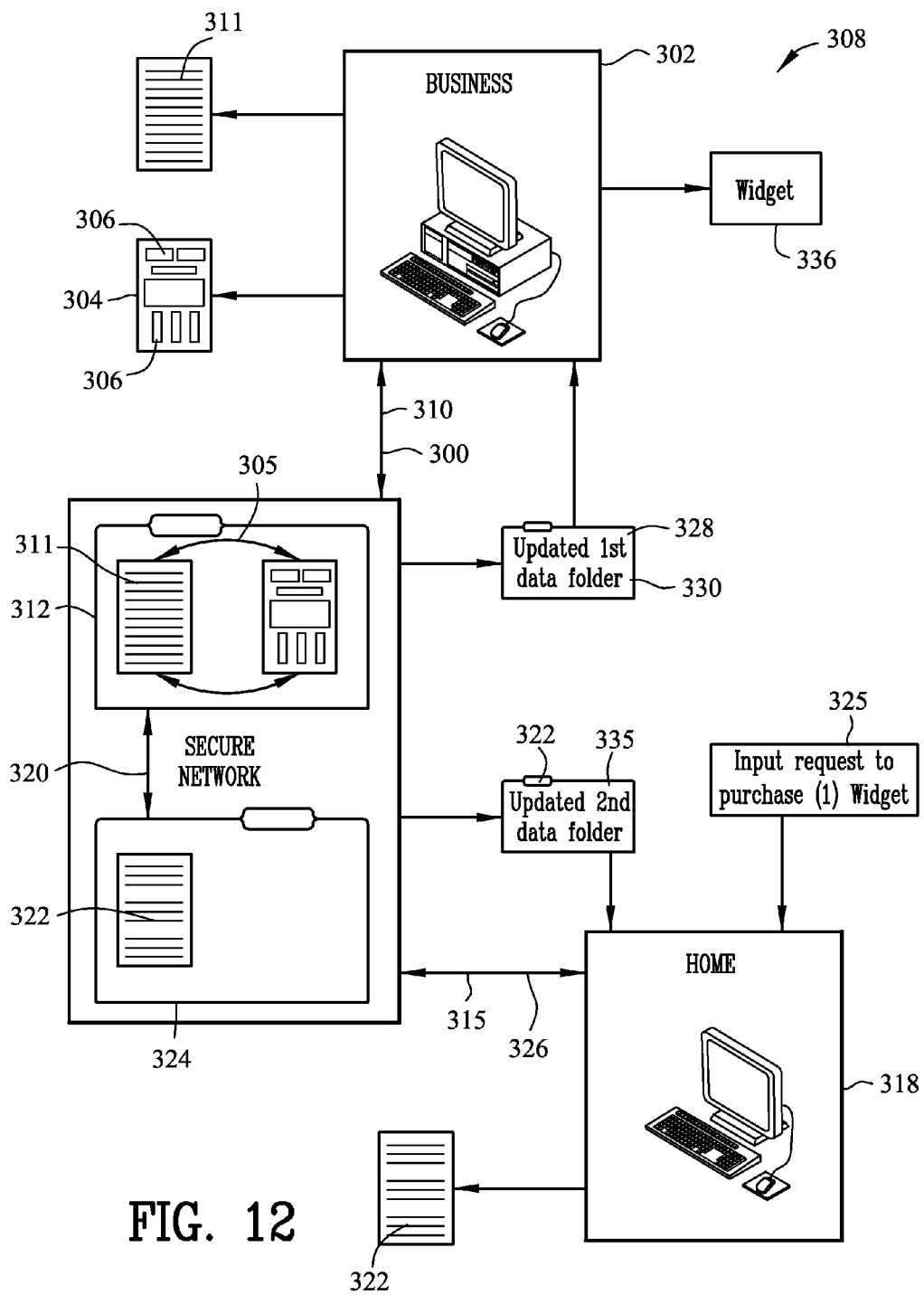
FIG. 12 is a block diagram of FIG. 11.

FIGS. 11 and 12 illustrate another embodiment of the subject invention. FIGS. 11 and 12 illustrate an apparatus and method for conducting secure communications. The apparatus and method comprising the steps of enrolling 300 a first entity 302 having a first transaction form 304, including one or more data fields 306 into a secure network 308. The one or more data fields 306 are interlinked 305 with a corresponding one or more first record-keeping entries 311 of the first entity 302 for defining a first data folder 312.

The first data folder 312 is uploading 310 from the first entity 302 to the secure network 308. A second entity 318 is enrolling 315 into the secure network 308 for accessing the first data folder 312. The first data folder 312 is interlinked 320 with a corresponding one or more second record-keeping entries 322 of the second entity 318 for defining a second data folder 324.

A selection is inputted 325 from the second entity 318 and into the first data folder 312. The input 325 of the selection may include but not limited to, purchasing a product such as a widget 336 or a service such as a cleaning service. An updated first data folder 328 is transmitted 330 from the secure network 308 to the first entity 302 for incorporating the updated first data folder 328 into the one or more first record-keeping entries 311 of the first entity 302. An updated second data folder 332 is transmitted 335 from the secure network 308 to the second entity 318 for incorporating the updated second data folder 332 into the one or more second record-keeping entries 322 of the second entity 318.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. A network for secure transactions and communications, comprising:
    a transmission server assigning a unique serial number for each transmission to facilitate the use of a different encryption scheme, for the transmitting and controlling how the data is packaged and handled as it is sent over the secured socket layer connection to the network destination;
    a first access terminal for inputting an identity;
    an enrollment database for receiving, recording, searching and outputting said identity;
    an encounter database receiving said identity from said enrollment database for generating, storing and outputting an encounter number associated with said identity;
    a second access terminal for receiving said encounter number from said encounter database and inputting an order associated with said encounter number;
    a transaction database receiving and recording said order and said encounter number from said second access terminal for outputting a first data pack and a second data pack;
    said first data pack including an identity number of the supplier, a order details, a primary serial number created by said transmission server used to encrypt said first data pack to send said first data pack to said supplier terminal, said second data pack including said primary serial number associated with said first data pack, the encounter number, and the identity of the supplier;
    said encounter database receiving said second data pack from said transaction database for generating, storing and outputting a third data pack that it sends to said enrollment database;
    said third data pack including the identity number of the ordering party, the supplier's identity number is used by said enrollment database to generate a fourth data pack;
    said fourth data pack includes the supplier's identity number, the identity of the ordering party, a secondary serial number created by said transmission server to encrypt said fourth data pack to send it to said supplier terminal;
    said enrollment database sends said secondary serial number and the associated identity number to said encounter database in a fifth data pack to matched the primary and secondary serial numbers by their common identity number to create the first rule data set;
    said supplier's terminal upon receiving said fourth data pack stores it and initiates an inquiry to said encounter server;
    said inquiry data pack containing said supplier's identity number, and secondary serial number;
    said encounter server upon receiving said supplier's inquiry looks up the first data set containing said secondary serial number and sends said data set to said supplier terminal in a sixth data pack; and
    said supplier terminal matches serial numbers in said data set to said order records and said identity records.

2. A network for secure transactions as set forth in claim 1, wherein said identity includes a patient name;
    said first access terminal includes a computer terminal;
    said second access terminal includes a physician computer terminal;
    said order includes a medication prescription; and
    said supplier terminal includes a pharmacy computer terminal.

3. A network for secure transactions as set forth in claim 1, wherein said identity includes a financial account;
    said first access terminal includes a computer terminal;
    said second access terminal includes a financial computer terminal;
    said order includes a financial transaction; and
    said supplier terminal includes a financial intermediary computer terminal.

4. A network for secure transactions as set forth in claim 1, further including a second access terminal for inputting said identity for requesting access to an identity record;
    said enrollment database receiving said identity from said second access terminal for verifying enrollment of said identity; and
    said enrollment database outputting said identity record for said identity to said second access terminal.

5. A network for secure transactions as set forth in claim 1, further including a research database receiving, recording and searching said order for conducting research.

6. A network for secure transactions as set forth in claim 1, further including a government database receiving, recording and searching said order for conducting research and creating an early warning system.

7. A network for secure transactions as set forth in claim 1, wherein said identity includes a patient name;
    said first access terminal includes a physician computer terminal;
    said order includes a medication prescription;
    said supplier terminal includes a pharmacy computer terminal; and
    a research database receiving, recording and searching said medication prescription for conducting medical research without said identity.

8. A network for secure transactions as set forth in claim 1, wherein said identity includes a patient name;
    said first access terminal includes a physician computer terminal;
    said order includes a medication prescription;

said supplier terminal includes a pharmacy computer terminal; and a government database receiving, recording and searching said order for creating an early warning or pandemic system.

9. A network for secure transactions and communications, comprising:
   a transmission server assigning a unique serial number for each transmission to facilitate the use of a different encryption scheme, transmitting and controlling how the data is packaged and handled as it is sent over the secured socket layer connection to it's network destination;
   a first access terminal for inputting an identity;
   an enrollment database for receiving, recording, searching and outputting said identity;
   an encounter database receiving said identity from said enrollment database for generating, storing and outputting an encounter number associated with said identity;
   a second access terminal for receiving said encounter number from said encounter database and inputting an order associated with said encounter number;
   a transaction database receiving and recording said order and said encounter number from said second access terminal for outputting a first data pack and a second data pack;
   said transmission server issues a serial number in the process of encrypting the first data pack used in the body of the first and second data packs and refers to it as serial B;
   said first data pack including the identity of said supplier, said order details, serial B is sent to said supplier terminal;
   said supplier terminal receives and records serial B and said order details;
   said second data pack including serial B, the encounter number, and the identity of the supplier is sent to said encounter database;
   said encounter database receives said second data pack looks up said encounter number to access associated supplier identity to create a third data pack;
   said third data pack includes the identity of the supplier, the identity of the ordering party that it sends to said enrollment database;
   said enrollment database uses said third data pack to create a fourth data pack and a fifth data pack;
   said transmission server issues a serial number in the process of encrypting the fourth data pack used in the body of the fourth and fifth data packs and refers to it as serial A;
   said fourth data pack includes the supplier's identity number, the identity of the ordering party, serial A and sends it to said supplier terminal;
   said fifth data pack including said serial A, the supplier's identity number and the identity of the ordering party is sent to from said enrollment database to said encounter database;
   said encounter database uses the supplier's identity from said fifth data pack and said second data pack to matched serial A with serial B to create said first rule data set;
   said supplier's terminal stores the fourth data pack and initiates an inquiry to said encounter server;
   said inquiry data pack includes serial A from said fourth data pack and the supplier's identity number;
   said encounter server receives said inquiry data pack, looks up said first data set that matches the serial A number and generates the sixth data pack;
   said sixth data pack contains the data set serial A and B number that it sends to said supplier's terminal that extracts serial A and serial B numbers to match said order details and said identity information; said supplier processes said order and sends serial B and the date the order was processes to said transaction server; and
   said transaction server receives and records said processing date and sends a notification of the date processed to either the first access terminal at the enrolled establishment or the enrolled customer's terminal.

10. A network for secure transactions and communications, comprising:
    a transmission server assigning a unique serial number for each transmission to facilitate the use of a different encryption scheme, for transmitting and controlling how the data is packaged and handled as it is sent over the secured socket layer connection to it's network destination;
    a first access terminal for inputting an identity located at an enrolled establishment;
    a second access terminal located at an enrolled customers location for entering an identity;
    a supplier terminal located at the establishment of an enrolled supplier to receive the secure transaction communications;
    an enrollment database for receiving, recording, searching and outputting said identity of an enrolled customer from an enrolled establishment;
    an encounter database receiving said identity from said enrollment database for generating, storing and outputting an encounter number associated with said identity to the first access terminal in the enrolled establishment for receiving said encounter number from said encounter database and inputting an order associated with said encounter number;
    a transaction database receiving and recording said order and said encounter number from said first access terminal for outputting a first data pack and a second data pack;
    said transmission server issues a serial number in the process of encrypting the first data pack that is recorded in the body of the first and second data packs and is referred to it as serial B;
    said first data pack includes the identity of said supplier, said order details, serial B is send to said supplier terminal;
    said supplier terminal receives and records serial B and said order details,
    said second data pack including serial B; the encounter number, and the identity of the supplier is sent to said encounter database;
    said encounter database receives said second data pack looks up said encounter number to access associated supplier identity to create a third data pack;
    said third data pack includes the identity of the supplier, the identity of the ordering party that it sends to said enrollment database;
    said enrollment database uses said third data pack to create a fourth data pack and a fifth data pack;
    said transmission server issues a serial number in the process of encrypting the fourth data pack used in the body of the fourth and fifth data packs and refers to it as serial A;
    said fourth data pack includes the supplier's identity number, the identity of the ordering party, serial A and sends it to said supplier terminal;

said fifth data pack including said serial A, the supplier's identity number and the identity of the ordering party is sent to from said enrollment database to said encounter database;

said encounter database uses the supplier's identity from said fifth data pack and said second data pack to matched serial A with serial B to create said first rule data set;

said supplier's terminal stores the fourth data pack and initiates an inquiry to said encounter server;

said inquiry data pack includes serial A from said fourth data pack and the supplier's identity number;

said encounter server receives said inquiry data pack, looks up said first data set that matches the serial A number and generates the sixth data pack;

said sixth data pack contains the data set serial A and B number that it sends to said supplier's terminal that extracts serial A and serial B numbers to match said order details and said identity information; said supplier processes said order and sends serial B and the date the order was processes to said transaction server;

said transaction server receives and records said processing date and sends a notification of the date processed to either the first access terminal at the enrolled establishment or the enrolled customer's terminal;

said customer access terminal can be utilized to contact the enrollment server to authenticate said customer and allow them access to their transaction information; and said access will allow them to determine the status of pending orders, to review or copy any past orders or to access the inventions communication features to create new orders or initiate new contacts and or communications.

11. A network for secure transactions as set forth in claim 10, wherein said identity includes a patient name;
    said first access terminal includes a Physician computer terminal;
    said second access terminal includes a Patient computer terminal;
    said order includes a medication prescription; and
    said supplier terminal includes a pharmacy computer terminal.

12. A network for secure transactions as set forth in claim 10, wherein said identity includes a financial account;
    said first access terminal includes a Financial computer terminal;
    said second access terminal includes a financial computer terminal;
    said order includes a financial transaction; and
    said supplier terminal includes a financial intermediary computer terminal.

13. A network for secure transactions as set forth in claim 10, further including a second access terminal for inputting said identity for requesting access to an identity record;
    said enrollment database receiving said identity from said second access terminal for verifying enrollment of said identity; and
    said enrollment database outputting said identity record for said identity to said second access terminal or to where second access terminal directs the records sent.

14. A network for secure transactions as set forth in claim 10, further including a research database receiving, recording and searching said orders and profile information for conducting research.

15. A network for secure transactions as set forth in claim 10, further including a government database receiving, recording and searching said orders and profile information for conducting research and creating an early warning system.

16. A network for secure transactions as set forth in claim 10, wherein said identity includes a patient name;
    said first access terminal includes a Physician computer terminal;
    said second access terminal includes a Patient computer terminal;
    said order includes a medication prescription;
    said supplier terminal includes a pharmacy computer terminal; and
    a research database receiving, recording and searching said medication prescription for conducting medical research without said identity.

17. A network for secure transactions as set forth in claim 10, wherein said identity includes a patient name;
    said first access terminal includes a Physician computer terminal;
    said second access terminal includes a Patient computer terminal;
    said order includes a medication prescription;
    said supplier terminal includes a pharmacy computer terminal; and
    a government database receiving, recording and searching said orders and profile information for creating an early warning pandemic system.

18. A network for secure transactions and communications, comprising:
    a transmission server assigning unique serial numbers for each transmission that generate different encryption schemes and further controls the packaging and handling of data content as it is sent over a secured socket layer connection to a known network destination;
    a first access terminal for inputting an identity;
    an enrollment database for receiving, recording, searching and outputting said identity;
    an encounter database receiving said identity from said enrollment database for generating, storing and outputting an encounter number associated with said identity;
    a first access terminal for receiving said encounter number from said encounter database and inputting an order associated with said encounter number;
    a transaction database receiving and recording said order and said encounter number from said second access terminal for outputting a first data pack and a second data pack;
    said transmission server issues a serial number in the process of encrypting the first data pack that is recorded in the body of the first and second data packs and is referred to it as serial B;
    said first data pack includes the identity of said supplier, said order details, serial B is send to said supplier terminal;
    said supplier terminal receives and records serial B and said order details, said second data pack including serial B, the encounter number, and the identity of the supplier is sent to said encounter database;
    said encounter database receives said second data pack looks up said encounter number to access associated supplier identity to create a third data pack;
    said third data pack includes the identity of the supplier, the identity of the ordering party that it sends to said enrollment database;
    said enrollment database uses said third data pack to create a fourth data pack and a fifth data pack;

said transmission server issues a serial number in the process of encrypting the fourth data pack used in the body of the fourth and fifth data packs and refers to it as serial A;

said fourth data pack includes the supplier's identity number, the identity of the ordering party, serial A and sends it to said supplier terminal;

said fifth data pack including said serial A, the supplier's identity number and the identity of the ordering party is sent to from said enrollment database to said encounter database;

said encounter database uses the supplier's identity from said fifth data pack and said second data pack to matched serial A with serial B to create said first rule data set;

said supplier's terminal stores the fourth data pack and initiates an inquiry to said encounter server;

said inquiry data pack includes serial A from said fourth data pack and the supplier's identity number;

said encounter server receives said inquiry data pack, looks up said first data set that matches the serial A number and generates the sixth data pack;

said sixth data pack contains the data set serial A and B number that it sends to said supplier's terminal that extracts serial A and serial B numbers to match said order details and said identity information;

said supplier processes said order and sends serial B and the date the order was processes to said transaction server;

said transaction server receives and records said processing date and sends a notification of the date processed to either the first access terminal at the enrolled establishment or the enrolled customer's terminal.

19. A network for secure communications, comprising:

a transmission server assigning a unique serial number for each transmission to facilitate the use of a different encryption scheme, for transmitting and controlling how the data is packaged and handled as it is sent over the secured socket layer connection to it's network destination;

a first access/destination terminal for inputting an identity and receiving instructions to establish and send digital communications located at any enrolled establishment or enrolled customer;

a second access/destination terminal located at any other enrolled establishment or enrolled customer's location for entering an identity and receiving instructions to establish and receive digital communications;

an enrollment database for receiving, recording, searching and outputting said identity of an enrolled customer or establishment at the first access/destination terminal to initiate a digital communication and receiving, recording, searching the identity number of the second access terminal chosen to receive a digital communication;

an encounter database receiving said identity of said first access/destination terminal from said enrollment database for generating, storing and outputting an encounter number associated with said identity; back to said first access terminal of the enrolled customer or establishment for receiving said encounter number from said encounter database and inputting digital communication instructions associated with said encounter number and said second access/destination terminal identification number;

a transaction database receiving and recording said digital communication instructions, said encounter number and said second access/destination terminal identification number from said first access terminal for outputting a first data pack and a second data pack;

said transmission server issues a serial number in the process of encrypting the first data pack that is recorded in the body of the first and second data packs and is referred to it as serial B;

said first data pack includes the digital communication instruction request, the identity # of second access/destination terminal, and Serial B;

said second data pack includes said serial B, and said encounter number;

said encounter database receives the second data pack from said transaction database looks up the encounter number in the data pack to access the associated first access identity number stored in said encounter database when the encounter number was generated;

said encounter database sends a third data pack to said enrollment database;

said third data pack includes the identity number associated with the first access destination terminal, that is used by said enrollment database to generate a fourth data pack and a fifth data pack;

said transmission server issues a serial number in the process of encrypting the fourth data pack that is recorded in the body of the fourth and fifth data packs and is referred to it as serial A;

said fourth data pack includes the second access destination terminal identity number, serial A and it is sent to said second access destination terminal;

said enrollment database sends said serial A number and the associated identity number to the encounter database in the fifth data pack where it is matched by identity number to serial B to create the first rule data set;

said first rule data set contains said serial A and B numbers that match the digital communication request to the first access terminal that originated the communication request;

said second access destination terminal receives and stores said fourth data pack initiates an inquiry data pack to the encounter server;

said inquiry data pack contains said second access destination terminal's identity number and said serial A obtained in said fourth data pack;

said encounter server upon receiving said inquiry data pack locates said first data set that contains the matching serial A number referenced in said inquiry to send said data set to said second access destination terminal;

said second access destination terminal opens the data set combines the digital communication instruction request and the identity records that match said data set serial numbers, said enrolled customer or enterprise associated with said second access destination terminal processes said digital communication instructions per it's arranged communications protocols and sends serial B to the transaction data server along with it's communication protocol requirements;

said transaction data server finds the digital communication instruction request by matching the serial B numbers; said transaction data server sends said first access terminal at the establishment or customers location;

said communications protocols; said first access destination terminal initiates the communications protocols connecting both parties utilizing an encrypted stream of digitized data packages.

* * * * *